US 7,368,457 B2

(12) United States Patent
Josien

(10) Patent No.: US 7,368,457 B2
(45) Date of Patent: May 6, 2008

(54) BRIDGED N-ARYLSULFONYLPIPERIDINES AS GAMMA-SECRETASE INHIBITORS

(75) Inventor: Hubert B. Josien, Hoboken, NJ (US)

(73) Assignee: Schering Corporation, Kenilworth, NJ (US)

( * ) Notice: Subject to any disclaimer, the term of this patent is extended or adjusted under 35 U.S.C. 154(b) by 472 days.

(21) Appl. No.: 10/842,783

(22) Filed: May 11, 2004

(65) Prior Publication Data

US 2004/0229902 A1 Nov. 18, 2004

Related U.S. Application Data

(60) Provisional application No. 60/470,146, filed on May 13, 2003.

(51) Int. Cl.
A61K 31/44 (2006.01)
C07D 221/02 (2006.01)

(52) U.S. Cl. .................................. 514/291; 546/112

(58) Field of Classification Search ............... 514/291; 546/112
See application file for complete search history.

(56) References Cited

FOREIGN PATENT DOCUMENTS

| JP | 4-247081 | * | 9/1992 |
|---|---|---|---|
| WO | WO 00/50391 | | 8/2000 |

OTHER PUBLICATIONS

Wang et al. "High performance . . . " CA 116:91540 (1992).*
Goto et al. "Preparation of fivemenbered . . . " CA 118:213064 (1993).*
LeBlanc et al. "Production of . . . " CA 121:298388 (1994).*
Hooper et al. "Membrane protein secretases" CA 126:196601 (1997).*
Xia et al. "Relationship between . . . " CA 139:357800 (2003).*
Beal et al. "Degenerative disease of the nervous system" in Harris's principle of internal medicine, 12th ed. (1991) p. 2060-2062.*
Takeda et al. "Preparation of five membered . . . " CA 118:213064 (1993).*
Bancher et al. "Low prevalence of apolipoprotein . . . " CA 128:46764 (1997).*
Chui et al. "Transgenic mice . . . " CA 131:86371 (1999).*
Nielsen et al. "Novel potent ligands . . . " J. Med. chem. v.43, p. 2217-2226 (2000).*
Obici et al. "A novel ABPP mutation . . . " Ann. Neurology, v.58,639-644 (2005).*
Pear et al. "T-cell acute lymphoblastic . . . " Curr. Opin. Hematology v.11, p. 426-433 (2004).*
Fortini M. "gamma secretase mediated . . . " Nature Rev. mol. cell. biol. v.3, p. 673-684 (2002).*
PCT International Search Report dated May 11, 2004 for corresponding PCT Application No. PCT/US2004/014671.
Takefumi Momose; Shohgo Atarashi, Reaction of N-Benzenesulfonyl-9-Azabicyclo-[3.3.1]Nona-2,6-Diene with Diborane: Failure of Cyclic Hydroboration in the Intramolecularly Faced Diene System, *Heterocycles* vol. 6, No. 4 (1977) 469-474 ISSN 0385-5414.
Butcher, J., Alzheimer's amyloid hypothesis gains support, Science and Medicine, The Lancet, vol. 356, Dec. 23/30, 2000, p. 2161.
Hardy, J., et al., The Amyloid Hypothesis of Alzheimer's Disease: Progress and Problems on the Road to Therapeutics, Science's Compass Review, vol. 297, Jul. 19, 2002, pp. 353-356.
Hock, C., et al., Antibodies against β-Amyloid Slow Cognitive Decline in Alzheimer's Disease, Neuron, vol. 38, May 22, 2003, pp. 547-554.

* cited by examiner

*Primary Examiner*—Celia Chang
(74) *Attorney, Agent, or Firm*—Henry C. Jeanette

(57) ABSTRACT

In an embodiment, this invention discloses novel gamma secretase inhibitors of Formulae I:

Formula I wherein the various moieties are described herein. Also disclosed is a method of treating Alzheimer's disease using a compound of Formula I or a composition comprising the compound of Formula I.

22 Claims, No Drawings

BRIDGED N-ARYLSULFONYLPIPERIDINES AS GAMMA-SECRETASE INHIBITORS

CROSS REFERENCE TO RELATED APPLICATION

This application claims the benefit of U.S. Provisional Application No. 60/470,146, filed May 13, 2003.

BACKGROUND OF THE INVENTION

WO 00/50391, published Aug. 13, 2000, discloses compounds having a sulfonamide moiety that are useful for the treatment and prevention of Alzheimer's disease and other diseases relating to the deposition of amyloid protein.

In view of the present interest in the treatment or prevention of neurodegenerative diseases, such as Alzheimer's disease, a welcome contribution to the art would be compounds for use in such treatment or prevention. This invention provides such a contribution.

SUMMARY OF THE INVENTION

In one aspect, this invention provides novel compounds as inhibitors of gamma secretase, methods for preparing such compounds, pharmaceutical compositions comprising one or more such compounds, methods for preparing pharmaceutical formulations comprising one or more such compounds, and methods of treatment, prevention, inhibition or amelioration of one or more diseases associated with gamma secretase using such compounds or pharmaceutical compositions.

In one aspect, the present application discloses a compound, and/or pharmaceutically acceptable salts or solvates of said compound, said compound having the general structure shown in Formula I:

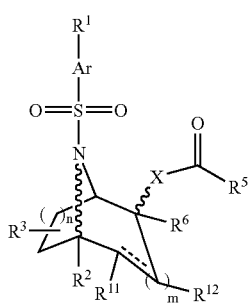

Formula I wherein:
Ar is aryl or heteroaryl;
X is O, NH, or $NR^6$;
m is 0, 1, 2 or 3, provided that when m=0 no double bond is present and when m>0 a double bond may or may not be present or a triple bond may or may not be present;
n is 0, 1, 2 or 3;
$R^1$ is 1 to 3 substituents independently selected from the group consisting of: hydrogen, alkyl, cycloalkyl, halogen, —$CF_3$, —$OCF_3$, —$NR^6R^7$, —CN, —$NO_2$, —$NH_2$, -alkylene-$NR^6R^7$, -alkylene-O-alkyl, —C(O)O-alkyl, —C(O)$NR^6R^7$, —N($R^6$)C(O)alkyl, —N($R^6$)C(O)cycloalkyl, —N($R^6$)C(O)aryl, —N($R^6$)C(O)heteroaryl, —N($R^6$)C(O)O-alkyl, —N($R^6$)C(O)$NR^6R^7$, —N($R^6$)S(O)$_2$alkyl, —OH, —O-alkyl, and —O-cycloalkyl;

$R^2$ is hydrogen, -alkyl, -cycloalkyl, -alkylene-cycloalkyl, -cycloalkyl, —$NR^6R^7$, -alkylene-$NR^6R^7$, -alkylene-O-alkyl, —O-alkyl, -heteroaryl, or -aryl;
$R^3$ is 1 to 6 substituents, which can be the same or different, each being independently selected from hydrogen, halogen, -alkyl, -cycloalkyl, —OH —$OCF_3$, —$CF_3$, —O-alkyl, —O-cycloalkyl, or —$NR^6R^7$;
$R^4$ is hydrogen, -alkyl, -cycloalkyl, -aryl or -heteroaryl; or $R^3$ and $R^4$ can be joined together to form a 3 to 6 member ring;
$R^5$ is —$NR^6R^7$, —N($R^6$)-alkylene-$NR^6R^7$, -alkyl, -cycloalkyl, -aryl -heteroaryl, -cycloalkyl, -alkylene-aryl, -alkylene-heteroaryl, -cycloalkylene-aryl, -cycloalkylene-heteroaryl, -heterocycloalkyl-aryl or -heterocycloalkyl-heteroaryl; or
$R^5$ is selected from the group consisting of:

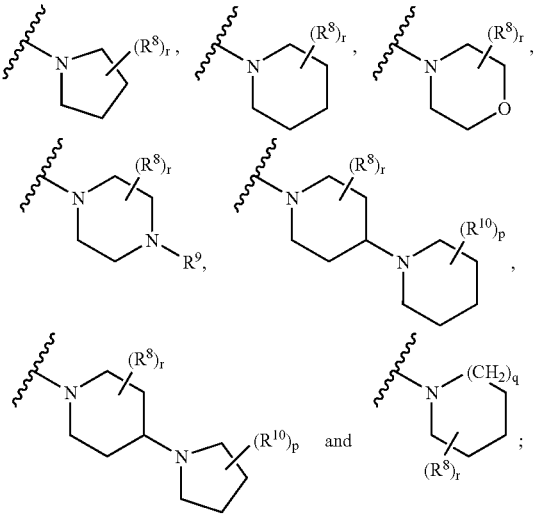

$R^6$ and $R^7$ can be the same or different, each being independently selected from the group consisting of: hydrogen, -aryl, heteroaryl, -alkyl, -cycloalkyl, -alkylene-aryl, -alkylene-heteroaryl,

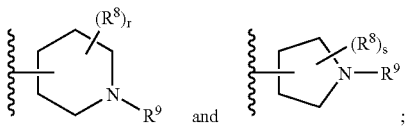

r is 0, 1, 2, 3 or 4;
s is 0, 1, 2 or 3;
$R^8$ is hydrogen, —OH, -alkyl, —C(O)$NR^6R^7$, —C(O)O-alkyl, or aryl, wherein said alkyl moiety may be unsubstituted or substituted with 1 to 4 hydroxy groups, and said aryl group may be unsubstituted or substituted with at least one substituent selected from the group consisting of alkyl, cycloalkyl, halogen, —$CF_3$, —$OCF_3$, —$NR^6R^7$, —CN, —$NO_2$, —$NH_2$, -alkylene-$NR^6R^7$, -alkylene-O-alkyl, —C(O)O-alkyl, —C(O)$NR^6R^7$, —N($R^6$)C(O)alkyl, —N($R^6$)C(O)cycloalkyl, —N($R^6$)C(O)aryl, —N($R^6$)C(O)heteroaryl, —N($R^6$)C(O)O-alkyl, —N($R^6$)C(O)$NR^6R^7$, —N($R^6$)S(O)$_2$alkyl, —OH, —O-alkyl, and —O-cycloalkyl;
$R^9$ is selected from the group consisting of: hydrogen, -alkyl, -cycloalkyl, -alkylene-aryl, -alkylene-heteroaryl, -alkyl-cycloalkyl, —C(O)O-alkyl, -alkylene-O-alkylene-OH, -aryl and -heteroaryl, wherein each said alkyl and cycloalkyl moieties may be independently substituted or unsubstituted and if substituted then substituted with 1 to 4 hydroxy groups or at least one —NR$^6$R$^7$ group;

each R$^{10}$ is independently selected from hydrogen or alkyl wherein said alkyl group may be substituted or unsubstituted and if substituted then R$^{10}$ is substituted with 1 to 4 hydroxy groups;

each R$^{11}$ and R$^{12}$ are independently selected from hydrogen, halogen, -alkyl, -cycloalkyl, —OH, —OCF$_3$, —CF$_3$, —O-alkyl, —O-cycloalkyl, —NR$^6$R$^7$ or aryl; or R$^{11}$ and R$^{12}$, together with the ring carbon atoms to which they are shown attached in Formula I, form a cycloalkyl ring, and wherein the cycloalkyl ring formed thereby can be unsubstituted or substituted with an alkyl, alkoxy, aryl, or halogen;

p is 0, 1, 2, 3 or 4; and q is 0, 1 or 2.

Unless specifically stated, the moieties alkyl, aryl, heteroaryl, cycloalkyl, alkylene and heterocycloalkyl (also referred to as heterocyclyl) in the above-noted definitions can be unsubstituted or each be optionally independently substituted with one or more suitable groups which can be the same or different and are independently selected. Non-limiting examples of such suitable groups as substituents are provided in the definitions that are in the Detailed Description section below. The possibility of such non-substitution as well as independent optional substitution in the moieties above is well within the scope of this invention.

This invention also provides a pharmaceutical composition comprising a therapeutically effective amount of one or more compounds of Formula I and one or more pharmaceutically acceptable carriers.

This invention also provides a method for inhibiting gamma-secretase comprising administering a therapeutically effective amount of one or more compounds of Formula I to a patient in need of such inhibition.

This invention also provides a method of treating one or more neurodegenerative diseases comprising administering a therapeutically effective amount of one or more compounds Formula I to a patient in need of treatment.

This invention also provides a method of inhibiting the deposition of amyloid protein (e.g., amyloid β protein) in, on, or around neurological tissue (e.g., the brain) comprising administering a therapeutically effective amount of one or more compounds of Formula I to a patient in need of treatment.

This invention also provides a method of treating Alzheimer's disease comprising administering a therapeutically effective amount of one or more compounds of Formula I to a patient in need of treatment.

DETAILED DESCRIPTION OF THE INVENTION

In one embodiment, the present application discloses a compound, or pharmaceutically acceptable salts or solvates of said compound, said compound having the general structure shown in Formula I.

In a preferred embodiment, Ar is aryl.

In another preferred embodiment, X is O.

In another preferred embodiment, m is 0 or 1.

In another preferred embodiment, n is 1 or 2.

In another preferred embodiment, R$^1$ is halogen.

In another preferred embodiment, R$^2$ is hydrogen.

In another preferred embodiment, R$^3$ is hydrogen.

In another preferred embodiment, R$^4$ is hydrogen or CH$_3$.

In another preferred embodiment, R$^5$ is: —NR$^6$R$^7$, —NR$^6$-alkylene-NR$^6$R$^7$,

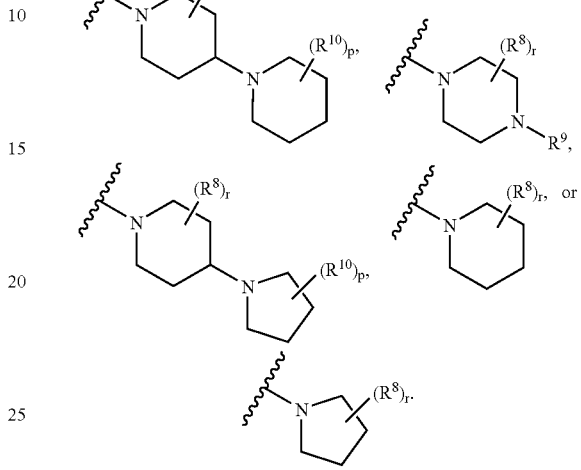

In an additional preferred embodiment, Ar is phenyl.

In an additional preferred embodiment, R$^1$ is 4-halo, more preferably 4-chloro.

In an additional preferred embodiment, R$^5$ is:

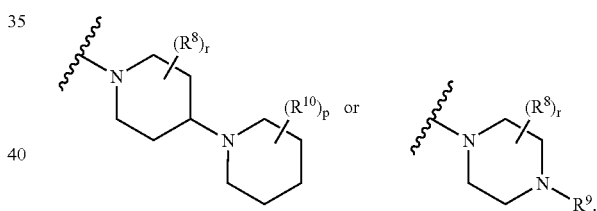

In an additional preferred embodiment, one double bond exists within a bicyclic ring in the structure represented by Formula I.

In an additional preferred embodiment, m=1 and n=2.

In an additional preferred embodiment, m=1 and n=1.

In an additional preferred embodiment, m=0 and n=1.

In an additional preferred embodiment, R$^5$ is

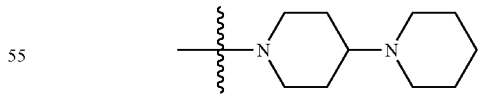

In an additional preferred embodiment, R$^{11}$ and R$^{12}$ are both H.

In an additional preferred embodiment, Ar is aryl;
X=O;
R$^1$ is halo;
R$^2$ is H;
R$^3$ is H;
R$^4$ is H; and
R$^5$ is:

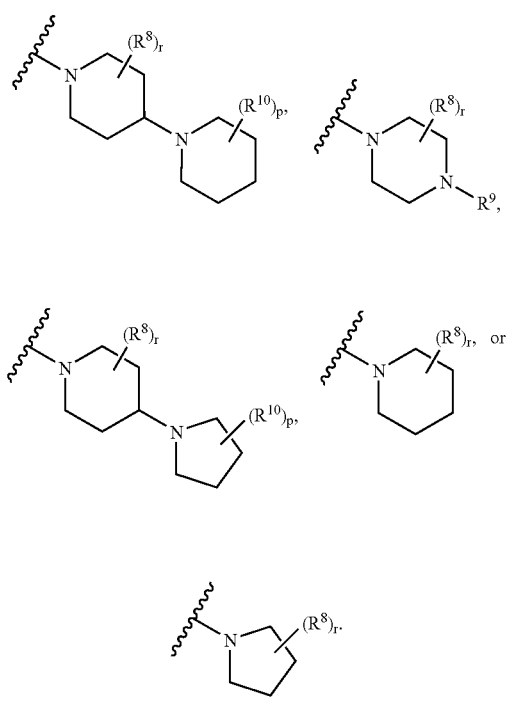
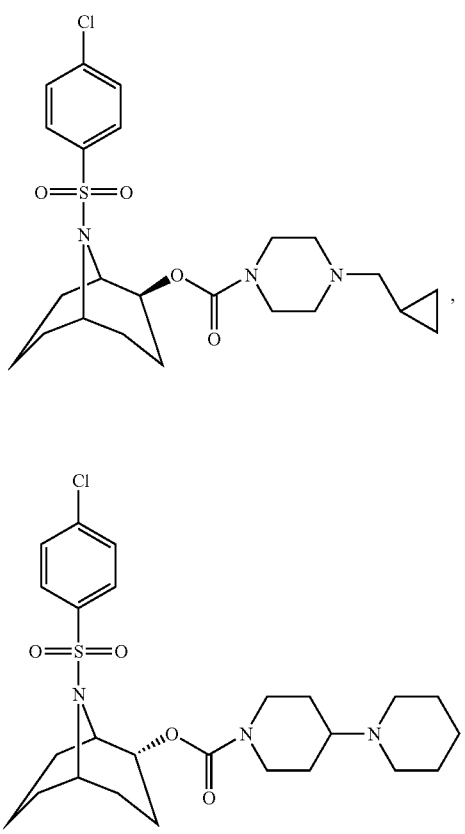
In an additional preferred embodiment, m is 1, no double or triple bond is present, and $R^{11}$ and $R^{12}$, together with the ring carbon atoms to which they are shown attached in Formula I, form a cyclopropyl ring.
Some preferred compounds of the invention include:
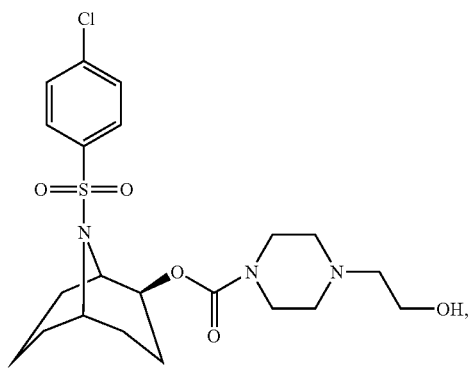
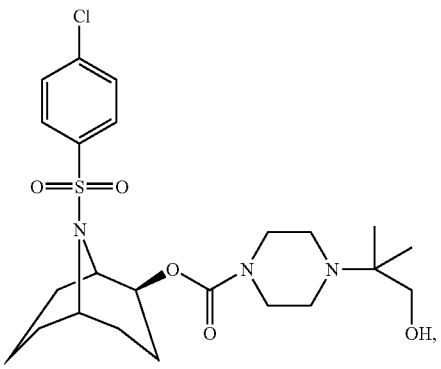
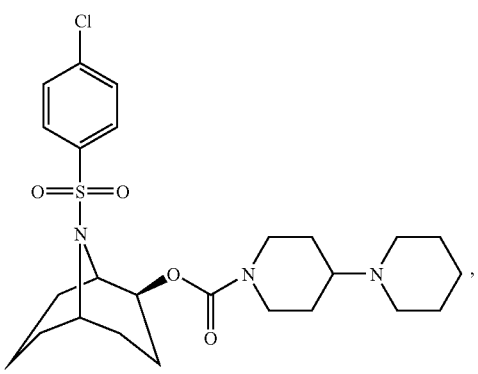
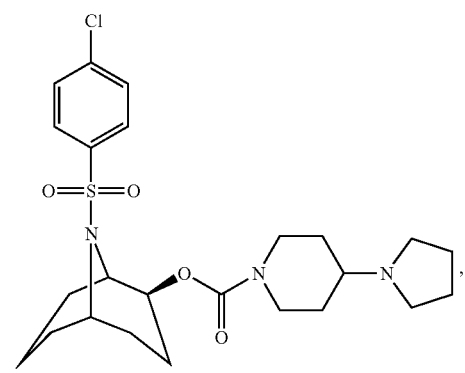

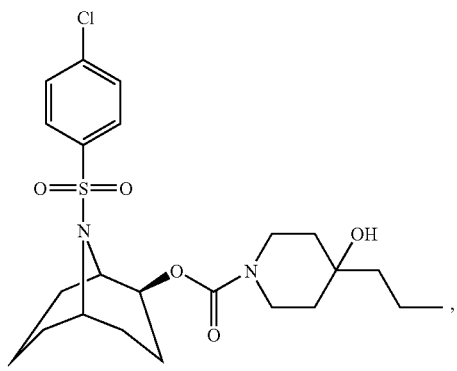
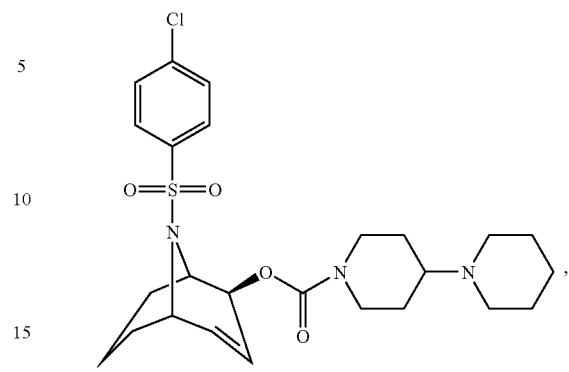
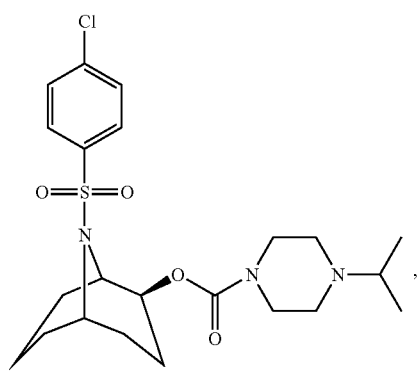
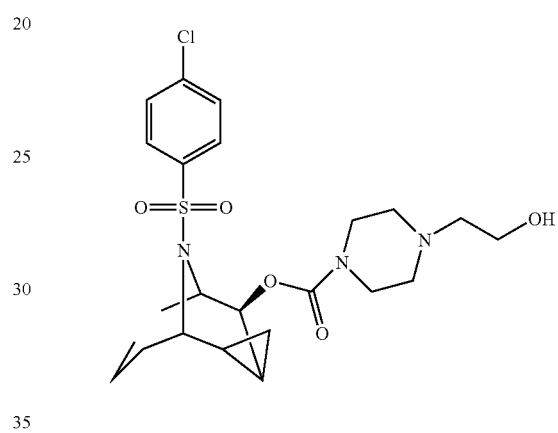
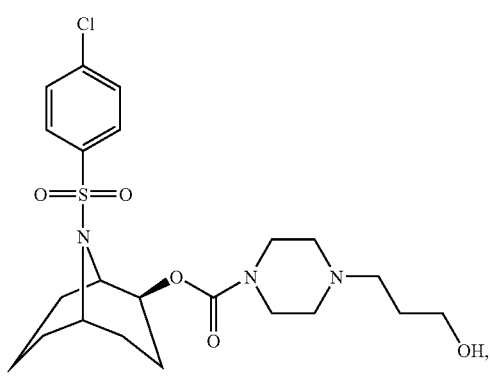
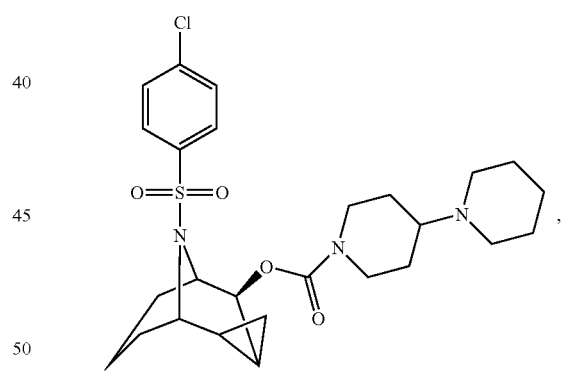
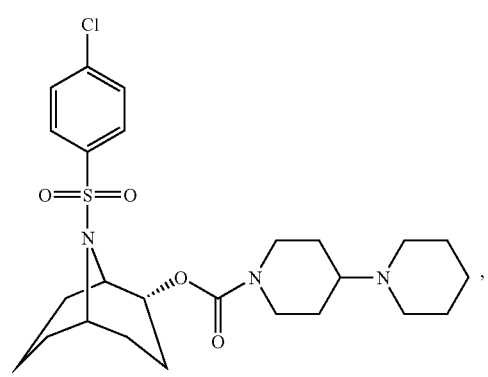
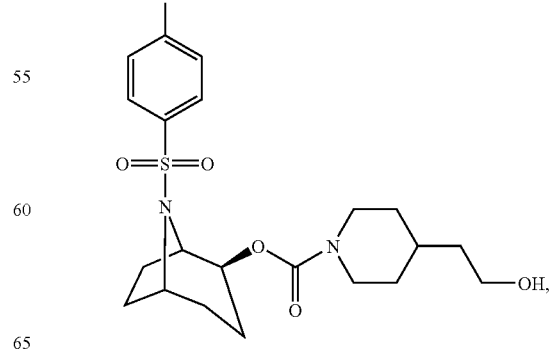

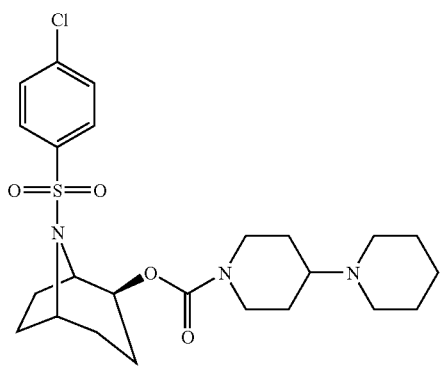
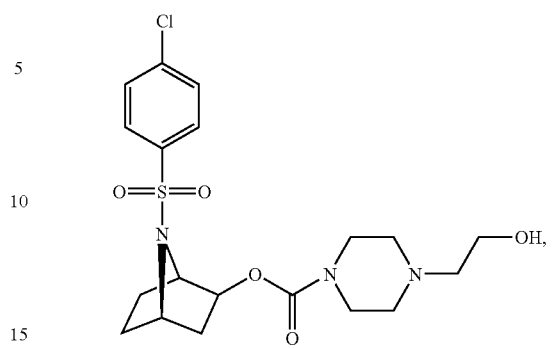
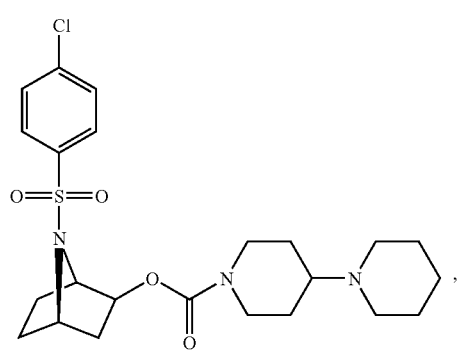
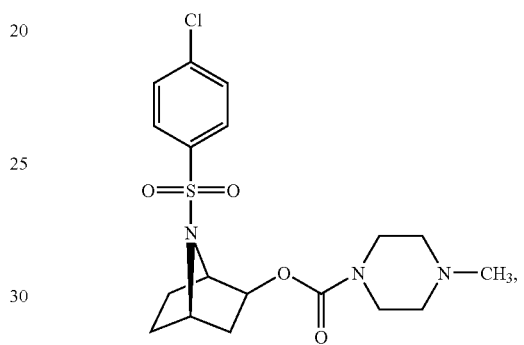
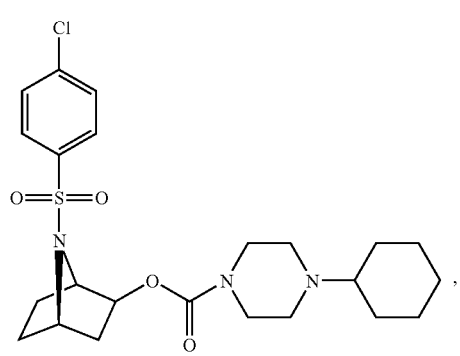
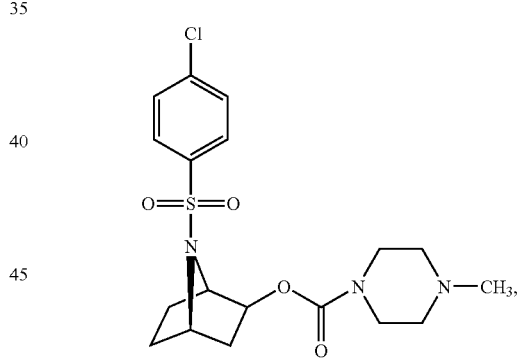
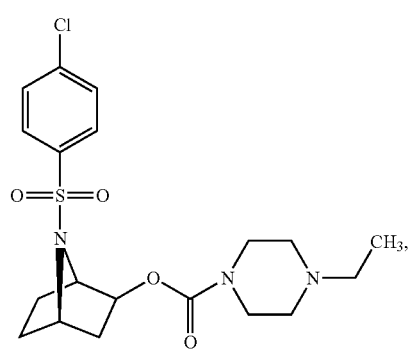
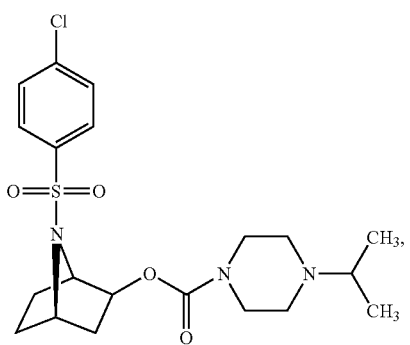

-continued

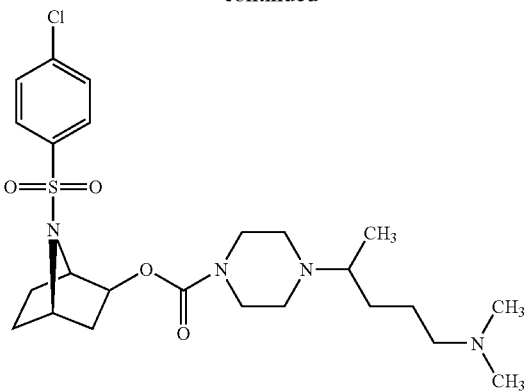

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "heteroarylalkyl", "—N(R$^6$)C(O)O-alkyl, etc.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, and alkoxy. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl. aryl and cycloalkyl.

"Alkylene" means a difunctional group obtained by removal of a hydrogen atom from an alkyl group that is defined above. Non-limiting examples of alkylene include methylene, ethylene and propylene.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Aryl" is sometimes referred to herein by the abbreviation "ar".

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. The abbreviation "cy" represents cyclohexyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl. "Ring system substituent" also means a cyclic ring of 3 to 7 ring atoms of which 1-2 may be a heteroatom, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

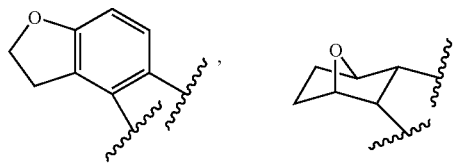

and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylcycloalkenyl" means a group derived from a fused aryl and cycloalkenyl in which the aryl and the cycloalkenyl ring share two ring carbon atoms. Preferred arylcycloalkenyls are those wherein aryl is phenyl and the cycloalkenyl consists of about 5 to about 6 ring atoms. The arylcycloalkenyl can be optionally substituted by one or more ring system substituents, wherein "ring system substituent" is as defined above. Non-limiting examples of suitable arylcycloalkenyls include 1,2-dihydronaphthalene, indene, and the like. The bond to the parent moiety is through a non-aromatic carbon atom.

"Cycloalkenylaryl" means a group derived from a fused arylcycloalkenyl as defined above. Non-limiting examples of suitable cycloalkenylaryls are as described herein for a arylcycloalkenyl, except that the bond to the parent moiety is through an aromatic carbon atom.

"Arylcycloalkyl" means a group derived from a fused aryl and cycloalkyl in which the aryl and the cycloalkyl ring share two ring carbon atoms. Preferred arylcycloalkyls are those wherein aryl is phenyl and the cycloalkyl consists of about 5 to about 6 ring atoms. The arylcycloalkyl can be optionally substituted by one or more ring system substituents, wherein "ring system substituent" is as defined above. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined above. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl in which the heteroaryl and cycloalkyl share two ring atoms. The shared ring atoms may both be carbon, or one of the shared ring atoms may be a heteroatom capable of bonding to at least 3 other atoms, such as nitrogen. Preferred heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The heteroarylcycloalkyl can be optionally substituted by one or more ring system substituents, wherein "ring system substituent" is as defined above. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 5,6,7,8-tetrahydroisoquinolyl, 5,6,7,8- tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like. The bond to the parent moiety is through a non-aromatic carbon atom.

"Cycloalkylheteroaryl" means a group derived from a fused beteroarylcycloalkyl as defined above. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkynyl" means an aryl-alkynyl- group in which the aryl and alkynyl are as previously described. Preferred aralkynyls contain a lower alkynyl group. The bond to the parent moiety is through the alkynyl. Non-limiting examples of suitable aralkynyl groups include phenacetylenyl and naphthylacetylenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Heteroaralkynyl" means an heteroaryl-alkynyl- group in which the heteroaryl and alkynyl are as previously described. Preferred heteroaralkynyls contain a lower alkynyl group. Non-limiting examples of suitable heteroaralkynyl groups include pyrid-3-ylacetylenyl and quinolin-3-ylacetylenyl. The bond to the parent moiety is through the alkynyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylamino" means an —NH$_2$ or —NH$_3^+$ group in which one or more of the hydrogen atoms on the nitrogen is replaced by an alkyl group as defined above.

"Arylamino" means an —NH$_2$ or —NH$_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O)$_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O)$_2$— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

Those skilled in the art will appreciate that the term "neurodegenerative disease" has its commonly accepted medical meaning and describes diseases and conditions resulting from abnormal function of neurons, including neuronal death and abnormal release of neurotransmitters or neurotoxic substances. In this instance it also includes all diseases resulting from abnormal levels of beta amyloid protein. Examples of such diseases include, but are not limited to, Alzheimer's disease, age-related dementia, cerebral or systemic amyloidosis, hereditary cerebral hemorrhage with amyloidosis, and Down's syndrome.

Lines drawn into the ring systems indicate that the indicated bond may be attached to any of the substitutable ring carbon atoms.

As is well known in the art, a bond drawn from a particular atom wherein no moiety is depicted at the terminal end of the bond indicates a methyl group bound through that bond to the atom. For example:

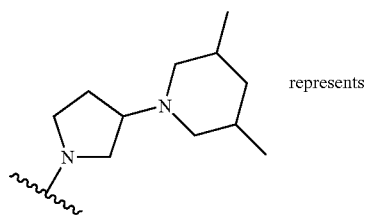 represents

-continued

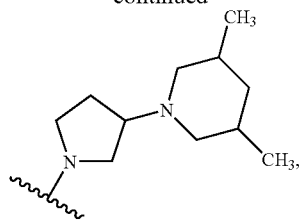

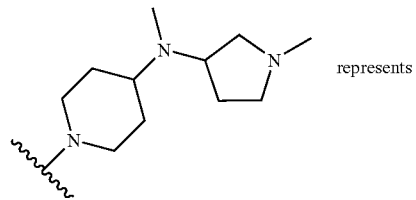 represents

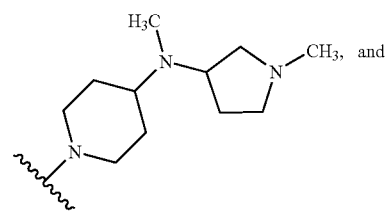 and

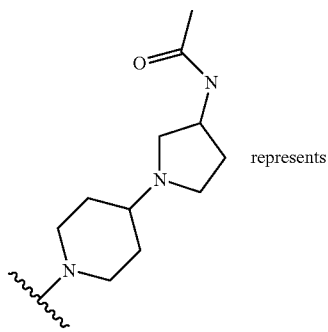 represents

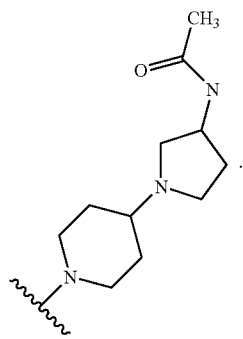

Those skilled in the art will appreciate a bicyclic ring structure, two examples of which are represented by the diagrams shown below. For convenience and description, carbon atoms can be numbered accordingly.

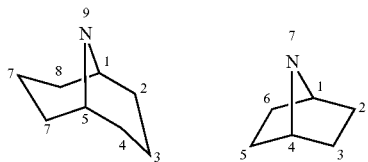

A dotted line within a ring structure, an example of which is shown in the diagram below, represents an optional bond or optional double bond. For example, with an optional bond,

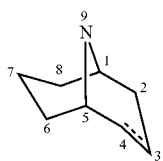

the structure above could represent the compound below:

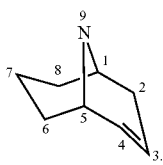

Further, the double or triple bond may form the bonds between any two available elements on any ring in the structure. For example, with a double bond forming,

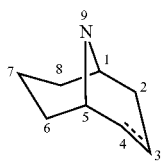

the structure above could represent the structure below:

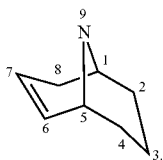

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting gamma secretase and thus producing the desired therapeutic effect.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula 1, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Polymorphic forms of the compounds of Formula I, and of the salts, solvates and/or prodrugs of the compounds of Formula I, are intended to be included in the present invention.

This invention is also directed to pharmaceutical compositions which comprise at least one compound of Formula I, or a pharmaceutically acceptable salt or solvate of said compound and at least one pharmaceutically acceptable carrier. Pharmaceutical compositions can comprise one or more of the compounds of Formula I.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

Another aspect of this invention is a kit comprising a therapeutically effective amount of at least one compound of Formula I, or a pharmaceutically acceptable salt or solvate of said compound and a pharmaceutically acceptable carrier, vehicle or diluent.

EXAMPLES

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Alltech platinum C18, 3 micron, 33 mm×7 mm ID; gradient flow: 0 min-10% $CH_3CN$ in water, 5 min-95% $CH_3CN$ in water, 7 min-95% $CH_3CN$ in water, 7.5 min-10% $CH_3CN$ in water, 9 min. The retention time and observed parent ion are given.

The following solvents and reagents may be referred to by their abbreviations in parenthesis:
AcOEt: represents ethyl acetate;
AcOH: represents acetic acid;
AIBN represents: 2.2'-azobisisobutyronitrile;
DCM: represents dichloromethane;
DCE: represents dichloroethylene;
DIBAH: represents diisobutylaluminum hydride;
DEAD: represents diethylazodicarboxylate;
DMF: represents dimethylformamide;
EDCI: represents 1-(3-dimethylaminopropyl)-3-ethylcarbodiimide;
$Et_2O$: represents diethyl ether;
EtOAc: represents ethyl acetate;
HOBT represents: 1-hydroxybenzotriazole;
LDA represents: lithium diisopropylamide;
MS: represents mass spectrometry;
Me: represents methyl;
MeOH: represents methanol;
NMO represents: N-methylmorpholine N-oxide;
NaOH: represents sodium hydroxide;
NMR: represents nuclear magnetic resonance;
HRMS: represents high resolution mass spectrometry;
OTBDMS: represents t-butyldimethylsilyloxy (or t-butyldimethylsilyl ether);
OTBDPS: represents t-butyldiphenylsilyloxy (or t-butyldiphenylsilyl ether);
P: represents a protecting group;
Ph: represents phenyl;
RT: represents room temperature.
TBAF: represents tetrabutylammonium fluoride;
TBDMS: represents represent t-butyldimethylsilyl;
TBDMSCl: represents t-butyldimethylsilyl chloride;
TBDPSCl: represents t-butyidiphenylsilylchloride;
TBS: represents t-butylsilyl;
TFA: represents trifluroacetic acid;
THF: represents tetrahydrofuran;
TMS: represents trimethylsilane;
TMSCl represents: trimethylsilyl chloride.

Compounds of Formula I can be prepared by various methods well known to those skilled in the art, and by the methods described below. The following methods are typical:

Method 1

In Method 1, compounds of Formula I having the structure A are prepared.

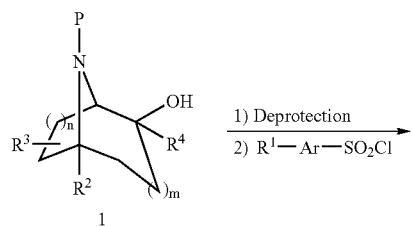

1

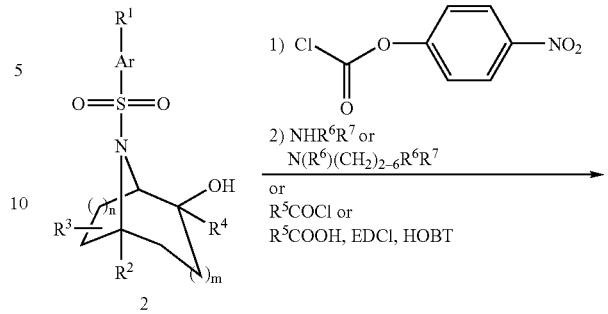

2

-continued

The protecting group in alcohol 1 is removed following standard conditions to lead to an amine that is further converted to alcohol 2 by reaction with a sulfonyl halide. Alcohol 2 can be converted to a variety of compounds of type A using methods well-known to those skilled in the art. For example, carbamates can be prepared by reaction of 2 with 4-nitrophenylchloroformate followed by reaction of the resulting carbonate with a primary or secondary amine. Alternatively, esters can be prepared by reaction of 2 with either an acid halide of a carboxylic acid in the presence of a suitable coupling reagent such as EDCI and HOBT.

Method 2

In Method 2, compounds of Formula I having the structure B are prepared.

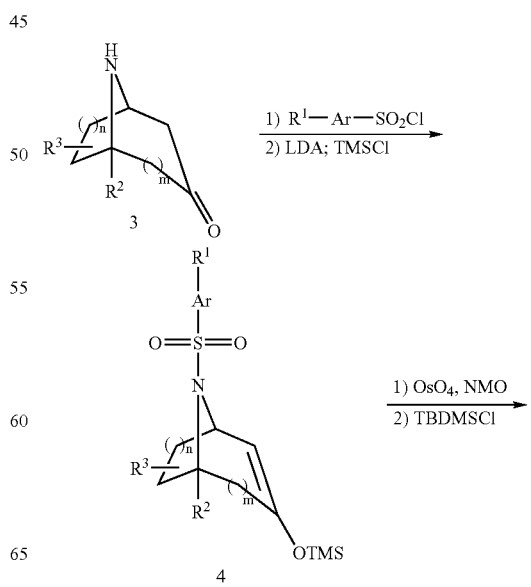

-continued

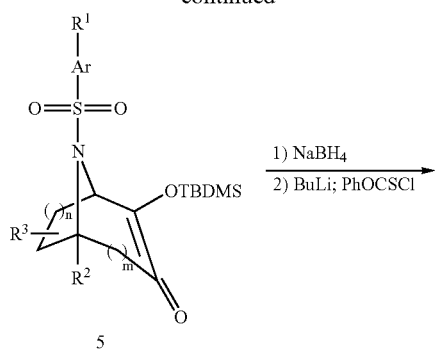

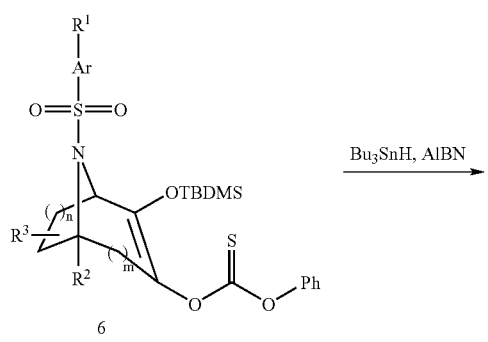

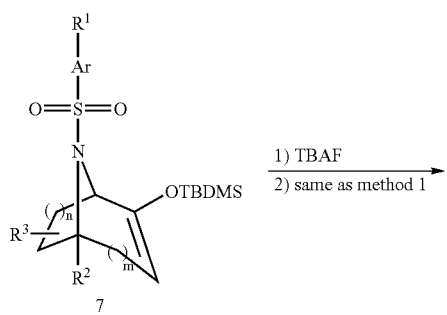

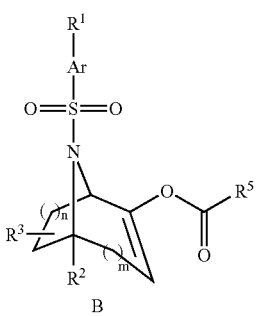

Cyclic amine 3 is converted to a sulfonamide by reaction with a sulfonyl halide, then converted to enol ether 4 using standard conditions such as deprotonation with LDA followed by reaction with TMSCl. Oxidation of enol ether 4 with an appropriate mixture of reagents such as osmium tetroxide and NMO followed by protection of the alcohol using a typical protecting group such as tert-butyldimethylsilyl chloride then gives ketone 5. Ketone 5 can be des-oxygenated to the alkylene 7 using a variety of methods known to those skilled in the art including but not limited to Wolf-Kishner type reactions and radical des-oxygenation reactions. For example, reaction of ketone 5 with an appropriate reducing agent such as sodium borohydride gives an alcohol which is then converted to thiocarbonate 6 using phenylchlorothioformate. Thiocarbonate 6 is then reduced to alkylene 7 with radical-induced reducing conditions such as AIBN with tributyltin hydride. The alcohol protecting group in alkylene 7 is then removed and the alcohol is converted to compounds of type B following methods described in Method 1.

Method 3

In Method 3, compounds of Formula I having the structure C are prepared.

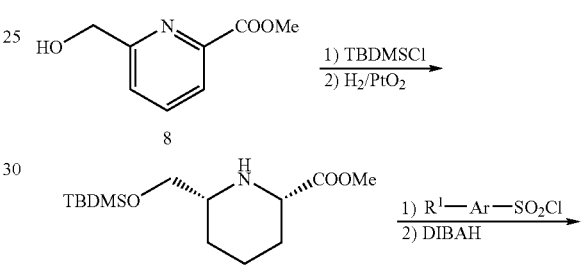

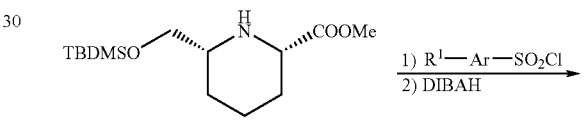

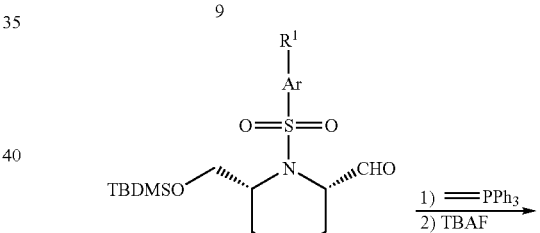

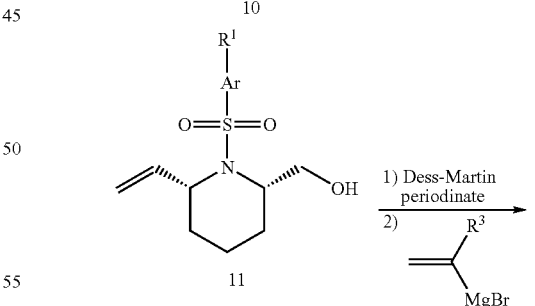

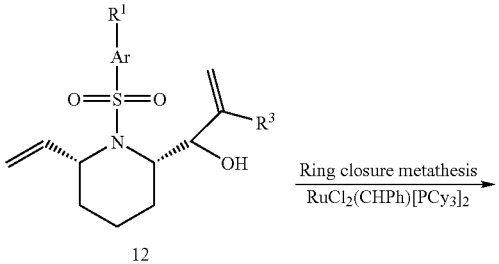

-continued

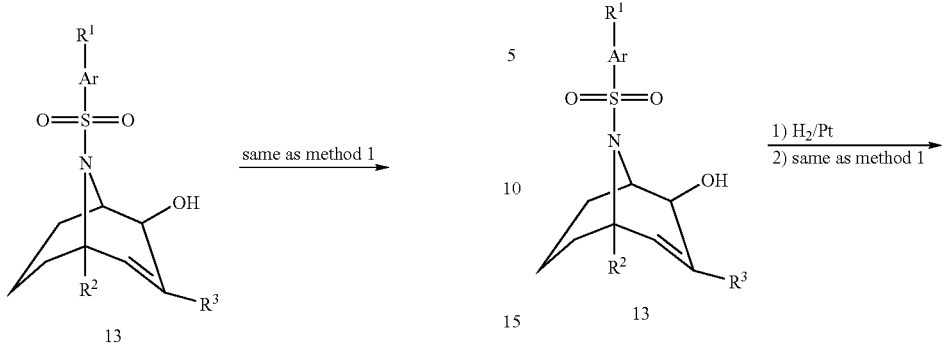

In Method 3, the alcohol functionality of methyl 2-(hydroxymethyl)-6-pyridinecarboxylate 8 is protected using a typical protecting group such as tert-butyldimethylsilyl chloride and the pyridine is then hydrogenated using a suitable catalyst such as platinum oxide, preferably in the presence of acetic acid, to give amine 9. Cyclic amine 9 is further converted to a sulfonamide by reaction with a sulfonyl halide, and then is reduced with a hydride reagent such as diisobutylaluminum hydride to give aldehyde 10. A Wittig reaction is then performed on aldehyde 10 and the alcohol protecting group is removed under standard conditions such as TBAF to give alcohol 11. The alcohol 11 is then oxidized to an aldehyde using an oxidative reagent such as Dess-Martin periodinate and the intermediate aldehyde is reacted with a metal-alkene such as a Grignard alkene to provide bis-alkene alcohol 12. A ring-closure-metathesis with a reagent such as $RuCl_2(CHPh)[PCy_3]_2$ (Grubbs's second generation catalyst) is then carried out on bis-alkene alcohol 12 to obtain bicyclic alcohol 13. Alcohol 13 is finally converted to compounds of type C following methods described in Method 1.

Method 4

In Method 4, compounds of Formula I having the structure D are prepared.

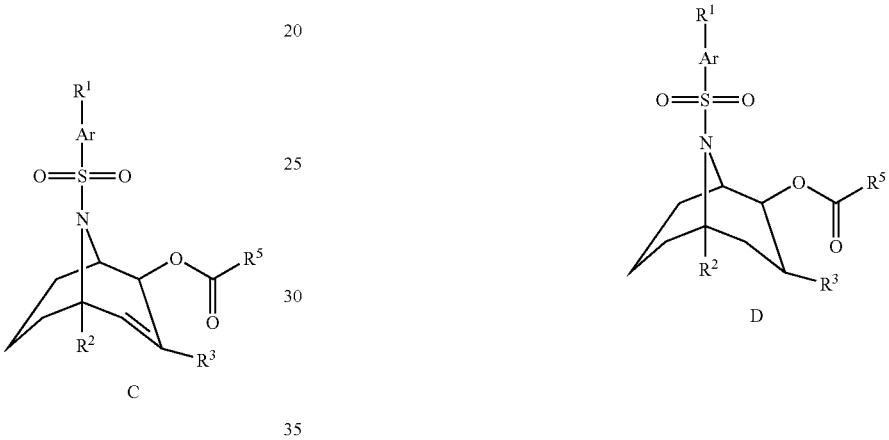

Alkene alcohol 13 is hydrogenated using a suitable catalyst such as platinum oxide, and the resulting alkyl alcohol is converted to compounds of type D using methods described in Method 1.

Preparative Example 1

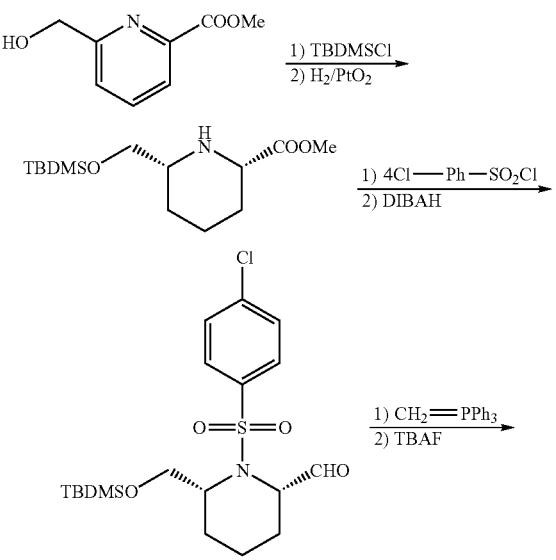

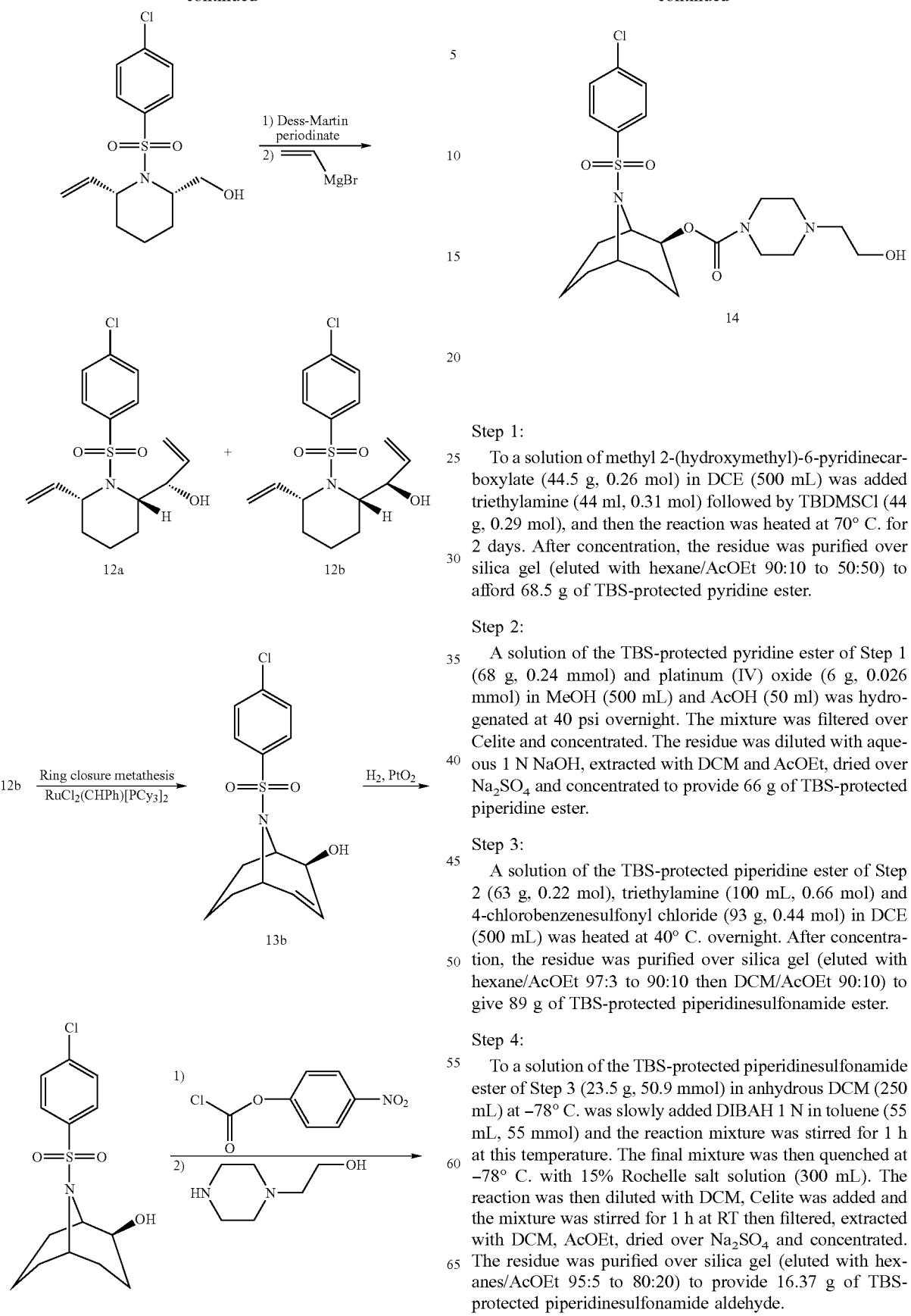

Step 1:

To a solution of methyl 2-(hydroxymethyl)-6-pyridinecarboxylate (44.5 g, 0.26 mol) in DCE (500 mL) was added triethylamine (44 ml, 0.31 mol) followed by TBDMSCl (44 g, 0.29 mol), and then the reaction was heated at 70° C. for 2 days. After concentration, the residue was purified over silica gel (eluted with hexane/AcOEt 90:10 to 50:50) to afford 68.5 g of TBS-protected pyridine ester.

Step 2:

A solution of the TBS-protected pyridine ester of Step 1 (68 g, 0.24 mmol) and platinum (IV) oxide (6 g, 0.026 mmol) in MeOH (500 mL) and AcOH (50 ml) was hydrogenated at 40 psi overnight. The mixture was filtered over Celite and concentrated. The residue was diluted with aqueous 1 N NaOH, extracted with DCM and AcOEt, dried over $Na_2SO_4$ and concentrated to provide 66 g of TBS-protected piperidine ester.

Step 3:

A solution of the TBS-protected piperidine ester of Step 2 (63 g, 0.22 mol), triethylamine (100 mL, 0.66 mol) and 4-chlorobenzenesulfonyl chloride (93 g, 0.44 mol) in DCE (500 mL) was heated at 40° C. overnight. After concentration, the residue was purified over silica gel (eluted with hexane/AcOEt 97:3 to 90:10 then DCM/AcOEt 90:10) to give 89 g of TBS-protected piperidinesulfonamide ester.

Step 4:

To a solution of the TBS-protected piperidinesulfonamide ester of Step 3 (23.5 g, 50.9 mmol) in anhydrous DCM (250 mL) at −78° C. was slowly added DIBAH 1 N in toluene (55 mL, 55 mmol) and the reaction mixture was stirred for 1 h at this temperature. The final mixture was then quenched at −78° C. with 15% Rochelle salt solution (300 mL). The reaction was then diluted with DCM, Celite was added and the mixture was stirred for 1 h at RT then filtered, extracted with DCM, AcOEt, dried over $Na_2SO_4$ and concentrated. The residue was purified over silica gel (eluted with hexanes/AcOEt 95:5 to 80:20) to provide 16.37 g of TBS-protected piperidinesulfonamide aldehyde.

Step 5:

To a solution of methyltriphenylphosphonium bromide (14.65 g, 41 mmol) in THF (150 mL) at −78° C. was added n-BuLi 2.5 N in hexanes (16.4 mL, 41 mmol) then the reaction was warmed to 0° C. It was then cooled to −78° C. and canulated into a solution of the TBS-protected piperidinesulfonamide aldehyde of Step 4 (16.35 g, 37.8 mmol) in THF (100 mL) at −78° C. The reaction was stirred for 30 min at −78° C. then for 30 min at RT. The final mixture was concentrated, diluted with aqueous 5% $NaHCO_3$ and DCM, extracted with DCM, dried over $Na_2SO_4$ and concentrated. Purification on silica gel (eluted with hexanes/AcOEt 95:5 to 80:20) afforded 9.81 g of TBS-protected alkene.

Step 6:

A solution of the TBS-protected alkene of Step 5 (9.81 g, 22.8 mmol) and TBAF 1N in THF (45 mL, 45 mmol) in THF (50 mL) was stirred at 50° C. for 1 h then concentrated. The residue was taken up in water, extracted with DCM, AcOEt, dried over $Na_2SO_4$ and concentrated. The residue was purified over silica gel (eluted with hexanes/AcOEt 80:20 to 60:40) to give 7.00 g of alkene alcohol.

Step 7:

To a solution of the alkene alcohol of Step 6 (7.00 g, 22.2 mmol) in DCM (100 mL) was added Dess-Martin periodinate (18.8 g, 44.4 mmol) and $NaHCO_3$ (5.59 g, 66.6 mmol). The solution was stirred for 3 h at RT then diluted with 5% $Na_2S_2O_3$ (400 mL), extracted with DCM, dried over $Na_2SO_4$ and concentrated. The residue was purified over silica gel (eluted with hexanes/AcOEt 95:5 to 80:20) to give 4.78 g of alkene aldehyde.

Step 8:

To a solution of the alkene aldehyde of Step 7 (3.68 g, 11.73 mmol) in THF (60 mL) at −40° C. was added vinyl magnesium bromide 1 N in hexanes (14 mL, 14 mmol) and the reaction was allowed to warm to −20° C. After 30 min at this temperature, the reaction was quenched with sat. aqueous $NH_4Cl$, extracted with DCM, AcOEt, dried over $Na_2SO_4$ and concentrated. The residue was purified over silica gel (eluted with hexanes/AcOEt 93:7 to 50:50) to provide, in order of elution, 540 mg of starting alkene aldehyde, 675 mg of bis-alkene alcohol isomer A (12a), and 2.63 g of bis-alkene alcohol isomer B (12b).

Step 9:

A solution of the bis-alkene alcohol isomer B of Step 8 (2.55 g, 7.46 mmol) in DCM (350 mL) was deaerated in vacuo then put under nitrogen. Bis(tricyclohexylphosphine) benzylidine ruthenium (IV) dichloride (930 mg, 1.11 mmol) was then added and the reaction was stirred at 50° C. overnight. The final solution was then concentrated and purified over silica gel (eluted with hexanes/AcOEt 85:15 to 40:60) to provide, in order of elution, 435 mg of starting material and 1.31 g of azabicyclo[3.3.1]nonane alkene alcohol.

Step 10:

A solution of the azabicyclo[3.3.1]nonane alkene alcohol of Step 9 (1.40 g, 4.46 mmol) and platinum (IV) oxide (215 mg) in AcOEt (30 mL) was hydrogenated at atmospheric pressure for 2 hours. The final mixture was filtered over Celite and concentrated. The residue was then purified over silica gel (eluted with hexanes/AcOEt 90:10 to 60:40) to afford 1.24 g of azabicyclo[3.3.1]nonane alcohol.

Step 11:

To a solution of the azabicyclo[3.3.1]nonane alcohol of Step 10 (170 mg, 0.54 mmol) in DCE (2.7 mL) was added p-nitrophenylchloroformate (217 mg, 1.10 mmol) followed by triethylamine (0.4 ml) and the reaction was stirred at RT overnight. After concentration, the residue was purified over silica gel (eluted with DCM) to obtain 192 mg of azabicyclo [3.3.1]nonane carbonate.

Step 12:

To a solution of azabicyclo[3.3.1]nonane carbonate (200 mg, 0.40 mmol) in DCE was added N-(2-hydroxyethyl) piperazine (0.1 ml, 0.80 mmol) and the reaction was heated at 50° C. overnight. The mixture was diluted with aqueous 0.5 NaOH, extracted with DCM and AcOEt and dried over $Na_2SO_4$. The residue obtained after concentration was purified over silica gel (eluted with DCM/MeOH 9:1) to give 40 mg of product of formula 14. $^1$H NMR ($CDCl_3$ 300 MHz) δ 7.76 (d, J=8.4 Hz, 2H), 7.43 (d, J=8.4 Hz, 2H), 4.77 (m, 1H), 4.28 (m,1H), 3.95 (m,1H), 3.55-3.70 (m, 4H), 3.35-3.55 (m, 2H), 2.40-2.65 (m, 8H), 1.45-1.90 (m, 9H); HRMS (MH$^+$) 472.1994.

Following similar procedures to those of Preparative Example 1 and using bis-alkene alcohol isomer A or bis-alkene alcohol isomer B (of Step 8) in the synthesis, the compounds in Table 1 were prepared:

TABLE 1

| Formula No. | COMPOUND | Mass Spec (M$^+$); retention time (min) |
| --- | --- | --- |
| 15 | [structure] | 510.1; 4.81 |

TABLE 1-continued
| Formula No. | COMPOUND | Mass Spec (M⁺); retention time (min) |
|---|---|---|
| 16 | 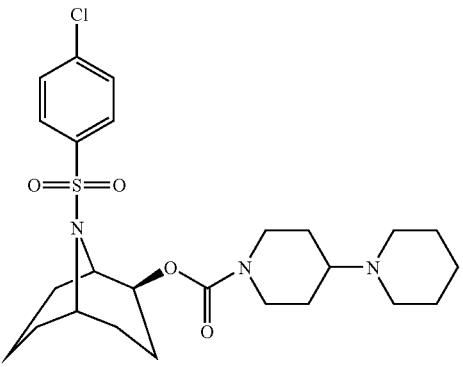 | 510.1; 4.78 |
| 17 | 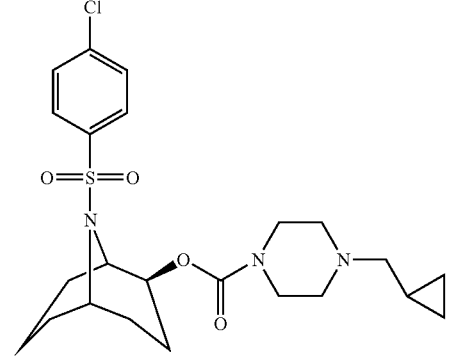 | 482.1; 4.45 |
| 18 | 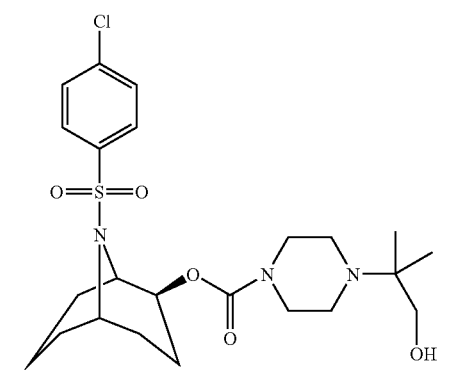 | 500.1; 4.23 |
| 19 | 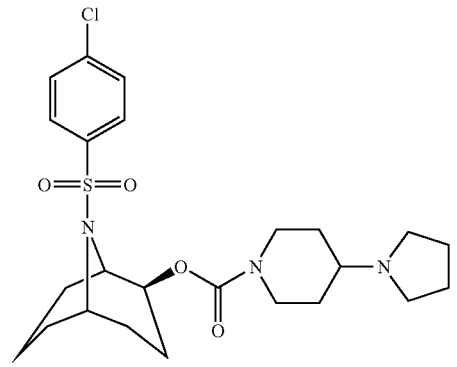 | 496.3; 3.27 |

TABLE 1-continued
| Formula No. | COMPOUND | Mass Spec (M+); retention time (min) |
|---|---|---|
| 20 | 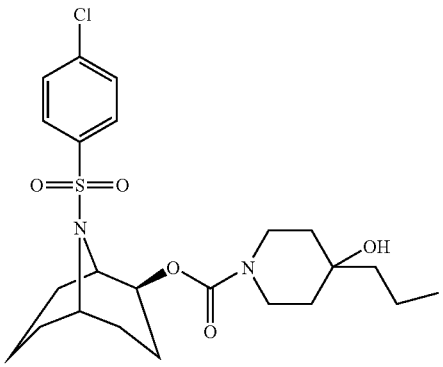 | 485.1; 4.70 |
| 21 | 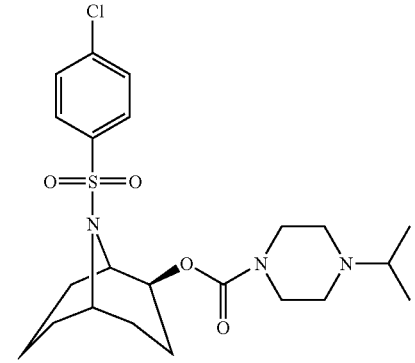 | 470.3; 3.21 |
| 22 | 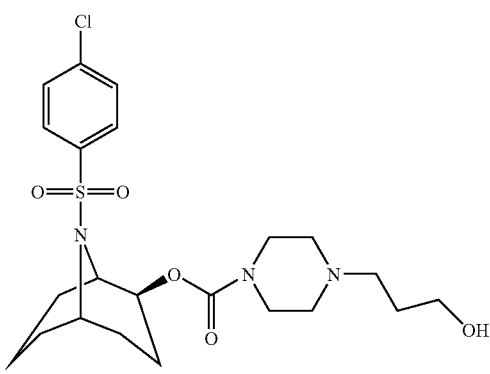 | 486.1; 4.23 |
| 23 | 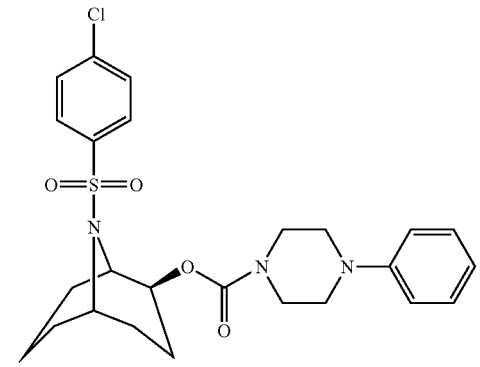 | 504.1; 5.23 |

TABLE 1-continued

| Formula No. | COMPOUND | Mass Spec (M⁺); retention time (min) |
|---|---|---|
| 24 | | 553.3; 3.22 |
| 25 | | 526.3; 3.28 |
| 26 | | 442.1; 4.43 |
| 27 | | 485.3; 3.17 |

TABLE 1-continued

| Formula No. | COMPOUND | Mass Spec (M⁺); retention time (min) |
| --- | --- | --- |
| 28 | | 443.2; 3.00 |
| 29 | | 478.3; 3.18 |
| 30 | | 439.2; 2.83 |
| 31 | | 439.2; 2.70 |

TABLE 1-continued

| Formula No. | COMPOUND | Mass Spec (M+); retention time (min) |
|---|---|---|
| 32 | | 492.3; 3.09 |

Preparative Example 2

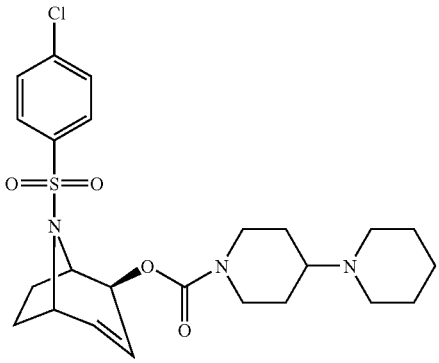

Formula 33

The alcohol of Preparative Example 1, Step 9 above, was subjected to conditions similar to those described in Preparative Example 1, Step 11 and Step 12, using 4-piperidinopiperidine instead of N-(2-hydroxyethyl) piperazine in the last step, to afford the desired product of formula 33. $^1$H NMR (CDCl$_3$ 300 MHz) δ 7.78 (d, J=8.4 Hz, 2H), 7.43 (d, J=8.4 Hz, 2H), 5.95-6.05 (m, 2H), 4.86 (br s, 1H), 4.10-4.45 (m, 3H), 3.75-4.05 (m, 1H), 2.40-2.85 (m, 8H), 1.30-2.00 (m, 15H); MS (ES) m/e 508.1 (M+H)$^+$; retention time: 5.35 min.

Following similar procedures to those of Preparative Example 2 and using bis-alkene alcohol isomer A in the synthesis, the following compound in Table 2 was prepared:

TABLE 2

| Formula No. | COMPOUND | Mass Spec (M+); retention time (min) |
|---|---|---|
| 34 | | 508.1; 5.52 |

Preparative Example 3

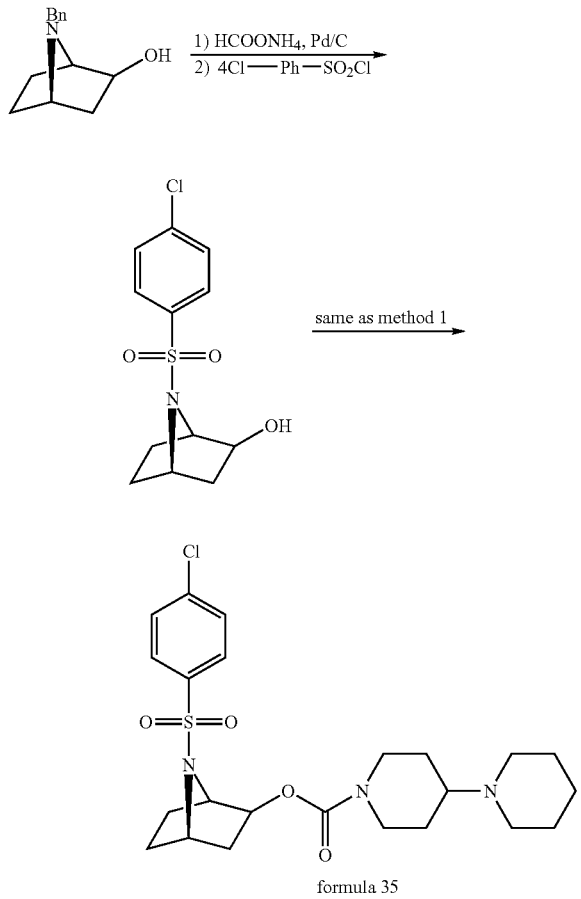

formula 35

Step 1:

A mixture of exo-7-benzyl-7-aza-bicyclo[2.2.1]heptan-2-ol (1.86 g, 9.1 mmol), ammonium formate (3.47 g, 55 mmol) and Pd/C 10% (200 mg) in MeOH (20 mL) was stirred for 2 h at 50° C. The solution was filtered over Celite, rinsed with MeOH and then 1 N HCl until a pH of 1 was obtained. The solution is then diluted with water, washed with $Et_2O$, and concentrated. The remaining solid (4.8 g) was taken up in 1 N NaOH (100 mL) and treated with 4-chlorobenzenesulfonyl chloride (10.55 g, 50 mmol) in DCM (40 mL) overnight. The mixture was diluted with water and DCM, extracted with DCM, dried over $Na_2SO_4$ and concentrated. Purification over silica gel (eluting with DCM/AcOEt 90:10 to 80:20) afforded 1.87 g of sulfonamide alcohol.

Step 2:

The product of Step 1 was subjected to conditions similar to the conditions described in Preparative Example 1, Step 11 and Step 12 above, using 4-piperidinopiperidine in the last step, to afford the desired product of formula 35.

$^1$H NMR (CDCl$_3$ 300 MHz) δ 7.81 (d, J=8.4 Hz, 2H), 7.42 (d, J=8.4 Hz, 2H), 4.64 (m, 1H), 3.90-4.25 (m, 4H), 2.55-2.75 (m, 2H), 2.30-2.55 (m, 5H), 1.65-1.95 (m, 6H), 1.50-1.60 (m, 4H), 1.30-1.45 (m, 6H); MS (ES) m/e 482.3 (M+H)$^+$; retention time: 3.71 min.

Following similar procedures to those of Preparative Example 3, the compounds of Table 3 were prepared:

TABLE 3

| Formula No. | COMPOUND | Mass Spec (M$^+$); retention time (min) |
|---|---|---|
| 36 | | 482.3; 4.06 |

TABLE 3-continued

| Formula No. | COMPOUND | Mass Spec (M⁺); retention time (min) |
|---|---|---|
| 37 | | 428.2; 3.64 |
| 38 | | 444.2; 3.38 |
| 39 | | 416.1; 3.94 |
| 40 | | 442.1; 4.48 |

TABLE 3-continued
| Formula No. | COMPOUND | Mass Spec (M+); retention time (min) |
|---|---|---|
| 41 | 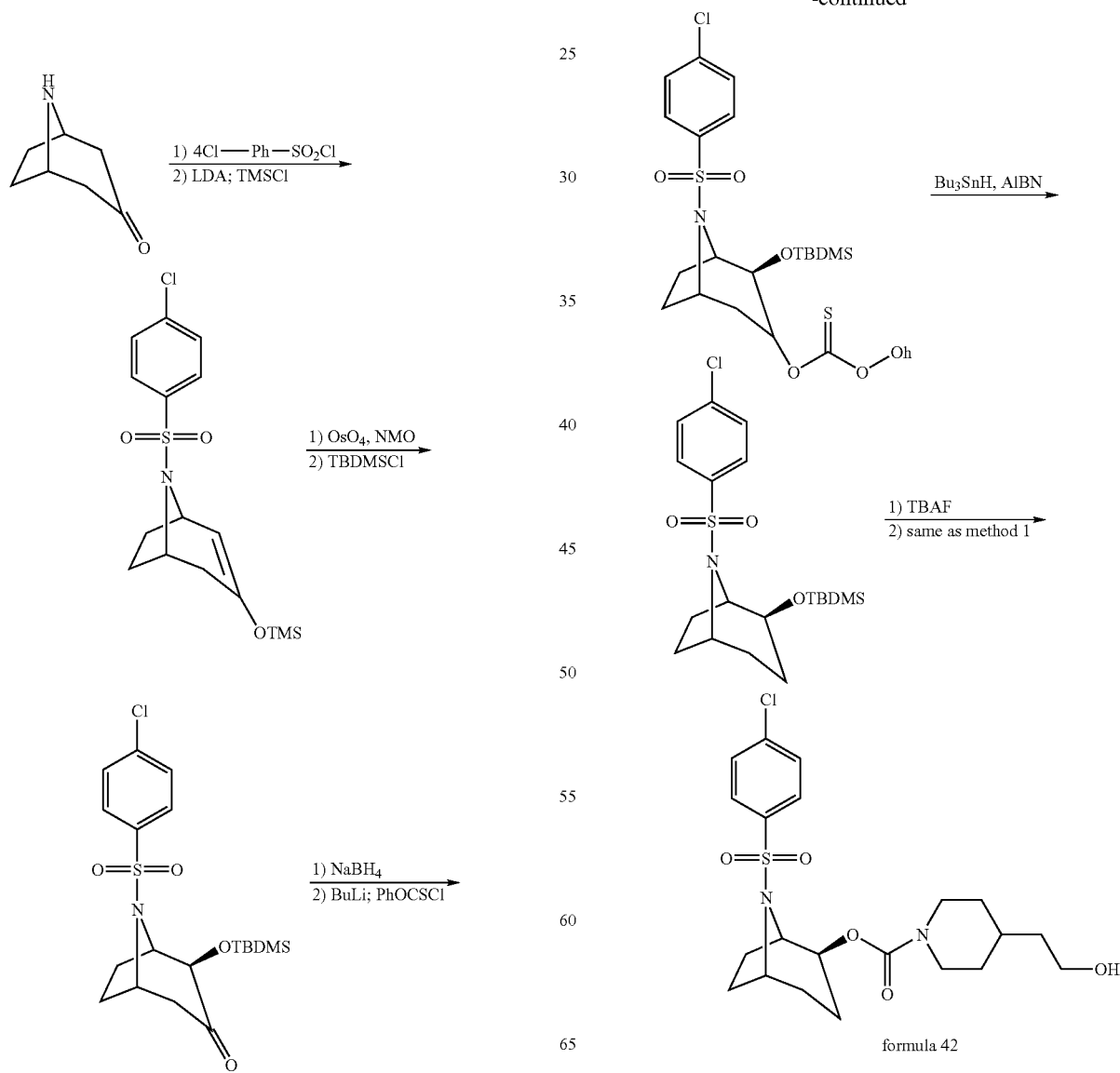 | 430.1; 4.41 |
Preparative Example 4

Step 1:
A solution of nor-tropinone hydrobromide (6.05 g, 29.5 mmol), 4-chlorobenzenesulfonyl chloride (6.65 g, 31.5 mmol), $K_2CO_3$ (9.70 g, 70 mmol) and tetrabutylammonium bromide (200 mg) in DCM (70 mL) and water (70 mL) was stirred at RT overnight. The mixture was extracted with DCM, dried over $Na_2SO_4$, concentrated and purified over silica gel (eluted with DCM/AcOEt 95:5) to give 9.04 g of nor-tropinone sulfonamide.

Step 2:
To a solution of LDA 2N in heptanes (16.1 mL, 32.2 mmol) in THF (120 mL) at −78° C. was slowly added a solution of the nor-tropinone sulfonamide of Step 1 (8.06 g, 26.9 mmol) in THF (160 mL) over 10 min. After 35 min at −78° C., chlorotrimethylsilane (6.8 mL) was added, the reaction was stirred 20 min at −78° C., saturated aqueous $NaHCO_3$ was added and the mixture was warmed to RT. After extraction with $Et_2O$, drying over $Na_2SO_4$, and concentration, the residue was purified over silica gel (eluted with hexanes/DCM 1:1 to DCM) to afford 3.88 g of nor-tropinone sulfonamide enol ether.

Step 3:
To a solution of the nor-tropinone sulfonamide enol ether of Step 2 (3.88 g, 10.43 mmol) and NMO (1.51 g, 12.9 mmol) in THF (40 mL) and water (15 mL) was added $OsO_4$ (100 mg, 0.40 mmol) at 0° C., and then the reaction was allowed to stir at RT overnight. After concentration, the solution was diluted with AcOEt and aqueous 10% $Na_2SO_3$, extracted with AcOEt, dried over $Na_2SO_4$ and concentrated. The residue was purified over silica gel (eluted with DCM/AcOEt 90:10 to 80:20) to afford 1.51 g of α-hydroxyketone sulfonamide.

Step 4:
A solution of the α-hydroxyketone sulfonamide of Step 3 (1.50 g, 4.75 mmol), TBDMSCI (860 mg, 5.70 mmol), and imidazole (390 mg, 5.70 mmol) in DMF (6 mL) was stirred overnight at 40° C. The cooled solution was diluted with water and $Et_2O$, extracted with $Et_2O$, dried over $Na_2SO_4$ and concentrated. The residue was purified over silica gel (eluted with hexane/DCM 1:1 to DCM) to provide 1.53 g of O-TBS ketone sulfonamide.

Step 5:
To a solution of the O-TBS ketone sulfonamide of Step 4 (1.53 g, 3.56 mmol) in MeOH (10 mL) at 0° C. was slowly added $NaBH_4$ (135 mg, 3.56 mmol) and the solution was stirred for 2 h at this temperature. The final mixture was concentrated, diluted with water, extracted with DCM and AcOEt, and dried over $Na_2SO_4$. The residue obtained after concentration was purified over silica gel (eluted with DCM to DCM/AcOEt 9:1) to afford 1.51 g of O-TBS alcohol sulfonamide.

Step 6:
To a solution of the O-TBS alcohol sulfonamide of Step 5 (1.10 g, 2.55 mmol) in THF (10 mL) at −78° C. was added n-BuLi 2.5 N in hexanes (1.10 mL, 2.80 mmol) followed, 1 min later, by phenylthionochloroformate (460 μL, 3.32 mmol). The reaction mixture was stirred 30 min at −78° C. then allowed to warm to RT and stirred for 1 h. The final solution was treated with 5% $NaHCO_3$, extracted with DCM (3×), AcOEt (1×), dried over $Na_2SO_4$ and concentrated. The residue was purified over silica gel (eluting with hexane/DCM 60:40 to DCM) to provide 1.34 g of O-TBS thiocarbonate sulfonamide.

Step 7:
A solution of the O-TBS thiocarbonate sulfonamide of Step 6 (1.34 g, 2.36 mmol), tributyltin hydride (1.35 mL, 5.0 mmol) and AIBN (107 mg, 0.65 mmol) was stirred under reflux for 6 h then concentrated. Purification of the crude over silica gel (eluted with hexane/DCM 60:40 to DCM) afforded 514 mg of O-TBS sulfonamide with other components.

Step 8:
A solution of the O-TBS sulfonamide of Step 7 (514 mg, 1.23 mmol) and TBAF 1 N in THF (2 mL, 2.0 mmol) in THF (3 mL) was stirred for 2 h at 40° C. then concentrated. Workup with aqueous saturated $NH_4Cl$, DCM, and AcOEt afforded a residue that was purified over silica gel (eluted with DCM/AcOEt 88:12 to 85:15) to give 105 mg of alcohol sulfonamide.

Step 9:
The product of Step 8 was subjected to conditions similar to the conditions described in Example 1, Step 11 and Step 12, using N-(2-hydroxyethyl)-piperazine in the last step, to afford the desired product of formula 42. $^1$H NMR ($CDCl_3$ 300 MHz) δ 7.77 (d, J=8.4 Hz, 2H), 7.43 (d, J=8.4 Hz, 2H), 4.59 (br s, 1H), 4.28 (br d, 2H), 3.30-3.70 (m,6H), 2.45-2.65 (m, 7H), 2.06 (m,1H), 1.40-1.85 (m, 7H); MS (ES) m/e 458.1 $(M+H)^+$; retention time: 3.65 min.

Following similar procedures to those of Preparative Example 4, the compound in Table 4 was prepared:

TABLE 4

| Formula No. | COMPOUND | Mass Spec ($M^+$); retention time (min) |
|---|---|---|
| 3 | 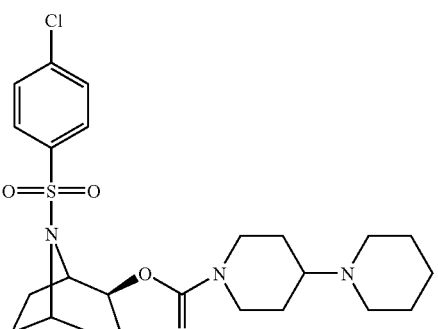 | 496.1; 4.36 |

Preparative Example 5

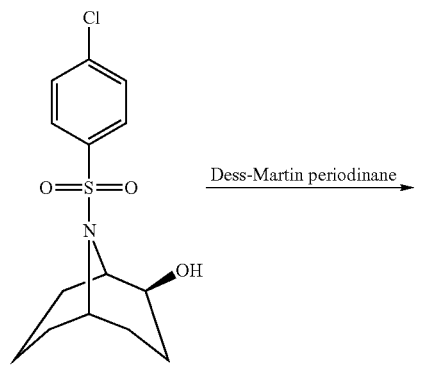

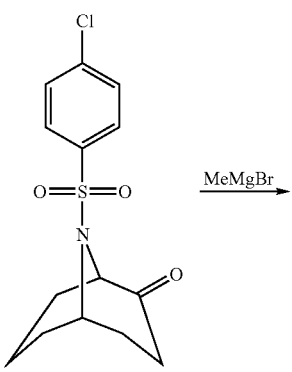

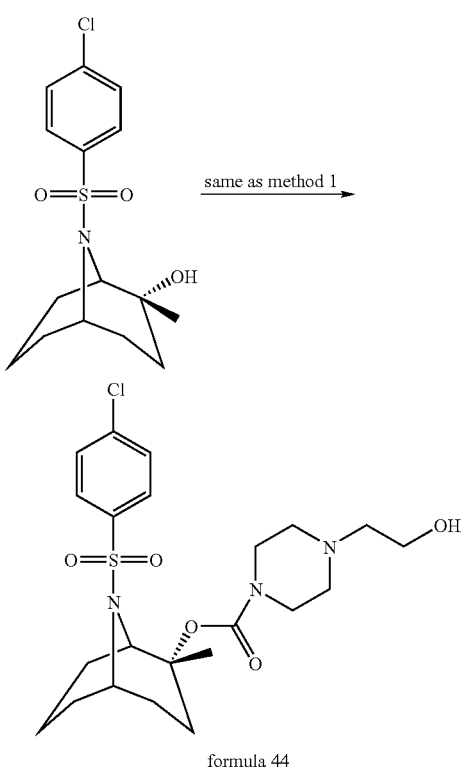

formula 44

Step 1:

A solution of the product alcohol of Preparative Example 1, Step 10 (450 mg, 1.42 mmol) and Dess-Martin periodinate (15% in DCM, 4.80 g, 1.70 mmol) in DCM (5 mL) was stirred at RT for 3 h. The mixture was treated with 5% sodium thiosulfate, extracted with DCM, dried over $Na_2SO_4$ and concentrated. The residue was purified over silica gel (eluted with hexanes/AcOEt 90:10 to 60:40) to give 460 mg of ketone.

Step 2:

To a solution of the ketone of Step 1 (150 mg, 0.48 mmol) in THF (3 mL) at −20° C. was slowly added MeMgBr 3N (190 µL, 0.56 mmol), and then the reaction was allowed to warm to 0° C. After 1 h, the final solution was poured into saturated $NH_4Cl$ and extracted with DCM, AcOEt, dried over $Na_2SO_4$ and concentrated. The residue was purified over silica gel (eluted with hexanes/AcOEt 90:10 to 60:40) to provide 125 mg of alcohol.

Step 3:

The product of Step 2 was subjected to conditions similar to the conditions described in Preparative Example 1, Step 11 and Step 12, using N-(2-hydroxyethyl)-piperazine in the last step, to afford the desired product of formula 44. $^1H$ NMR ($CDCl_3$ 300 MHz) δ 7.79 (d, J=8.4 Hz, 2H), 7.46 (d, J=8.4 Hz, 2H), 4.43 (m,1H), 4.08 (m,1H), 3.60-3.70 (m, 3H), 3.40-3.55 (m, 4H), 2.40-2.70 (m, 8H), 1.40-2.20 (m, 9H), 1.54 (s, 3H); MS (ES) m/e 486.1 $(M+H)^+$; retention time: 4.06 min.

Following similar procedures to those of Preparative Example 5, the compound of Table 5 was prepared:

TABLE 5

| Formula No. | COMPOUND | Mass Spec (M+); retention time (min) |
|---|---|---|
| 45 | (structure) | 524.1; 4.58 |

Preparative Example 6

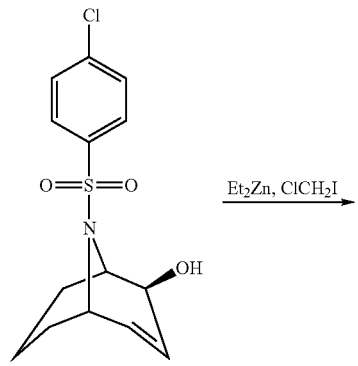

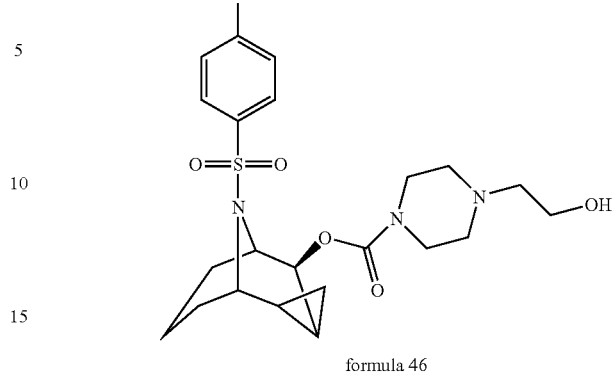

Step 1:

To a solution of diethylzinc (1 N in hexanes, 5 mL, 5 mmol) in DCE (20 mL) at −20° C. was slowly added chloroiodomethane (370 μL, 5 mmol), and the reaction was stirred for 5 min at this temperature. A solution of the product, the alcohol, of Preparative Example 1, Step 9 (740 mg, 2.36 mmol) in DCE (3 mL) was then added and the reaction was stirred for 1 h at −10° C. and for 1 h at RT. The final mixture was quenched into sat NH$_4$Cl, extracted with DCM, dried over Na$_2$SO$_4$ and concentrated. The crude product was purified over silica gel (eluted with hexanes/AcOEt 80:20 to 50:50) to give 512 mg of cyclopropyl alcohol.

Step 2:

The product of Step 1 was subjected to conditions similar to the conditions described in Preparative Example 1, Step 11 and Step 12, using N-(2-hydroxyethyl)-piperazine in the last step, to afford the desired product of formula 46. $^1$H NMR (CDCl$_3$ 300 MHz) δ 7.74 (d, J=8.4 Hz, 2H), 7.45 (d, J=8.4 Hz, 2H), 4.91 (d, J=7.5 Hz, 1H), 4.30 (br s, 1H), 3.90 (m, 1H), 3.63 (m, 2H), 3.30-3.55 (m, 4H), 2.40-2.60 (m, 8H), 1.90-2.10 (m, 1H), 1.35-1.70 (m, 8H), 0.98 (m, 1H), 0.50-0.62 (m, 2H); MS (ES) m/e 484.1 (M+H)$^+$; retention time: 4.28 min.

Following similar procedures to those of Preparative Example 6, the compounds in Table 6 were prepared:

TABLE 6

| Formula No. | COMPOUND | Mass Spec (M$^+$); retention time (min) |
|---|---|---|
| 47 | | 454.1; 4.44 |

TABLE 6-continued

| Formula No. | COMPOUND | Mass Spec (M+); retention time (min) |
|---|---|---|
| 48 | 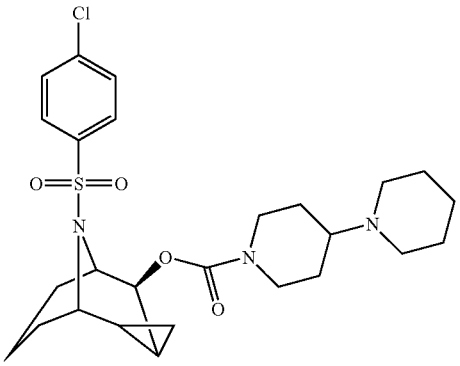 | 522.1; 4.95 |

Assay:

The pharmacological properties of the compounds of this invention may be confirmed by a number of pharmacological assays. The exemplified pharmacological assays which are described later have been carried out with the compounds according to the invention and their salts.

Gamma secretase activity was determined as described by Zhang et al. (*Biochemistry*, 40 (16), 5049-5055, 2001), which is herein incorporated by reference. Activity is expressed either as a percent inhibition or as the concentration of compound producing 50% inhibition of enzyme activity.

Reagents. Antibodies WO2, G2-10, and G2-11 were obtained from Dr. Konrad Beyreuther (University of Heidelberg, Heidelberg, Germany). WO2 recognizes residues 5-8 of Aβ peptide, while G2-10 and G2-11 recognize the specific C-terminal structure of Aβ 40 and Aβ 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, *Tissue Culture, and Cell Line Construction*. The construct SPC99-Lon, which contains the first 18 residues and the C-terminal 99 amino acids of APP carrying the London mutation, has been described (Zhang, L., Song, L., and Parker, E. (1999) *J. Biol. Chem.* 274, 8966-8972). Upon insertion into the membrane, the 17 amino acid signal peptide is processed, leaving an additional leucine at the N-terminus of Aβ SPC99-Ion was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for Aβ production by inducing C99 expression with 0.1 g/mL tetracycline for 16-20 h and analyzing conditioned media with a sandwich immunoassay (see below). One of the clones, designated as pTRE.15, was used in these studies.

Membrane Preparation. C99 expression in cells was induced with 0.1 g/mL tetracycline for 20 h. The cells were pretreated with 1 M phorbol 12-myristate 13-acetate (PMA) and 1 M brefeldin A (BFA) for 5-6 h at 37 C before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70 C before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70° C.

γ-Secretase Reaction and Aβ Analysis. To measure γ-secretase activity, membranes were incubated at 37° C. for 1 h in 50 μL of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2-10 and biotin-WO2, while Aβ 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

The compound of Example 16 had an $IC_{50}$ of about 16 nM. The compounds of Examples 18, 19, 20, 33 and 48 had an $IC_{50}$ within the range of about 50 nM to about 0.1 μM. The compounds of Examples 14, 17, 21, 22, 23, 24, 25, 26, 27, 28, 29, 34 and 43 had an $IC_{50}$ within the range of about 0.1 to about 1.0 μM. The compounds of Examples 15, 35, 36, 37 and 40 had an $IC_{50}$ within the range of about 1 to about 10 μM.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound, or pharmaceutically acceptable salts and/or solvates of said compound, said compound having the general structure shown in Formula I:

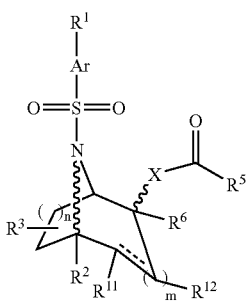

Formula I wherein:

Ar is aryl or heteroaryl;

X is O, NH, or $NR^6$;

m is 1 and a double bond may or may not be present or a triple bond may or may not be present;

n is 2;

$R^1$ is 1 to 3 substituents independently selected from the group consisting of: hydrogen, alkyl, cycloalkyl, halogen, —$CF_3$, —$OCF_3$, —$NR^6R^7$, —CN, —$NO_2$, -$NH_2$, -alkylene-$NR^6R^7$, -alkylene-O-alkyl, —C(O)O-alkyl, —C(O)$NR^6R^7$, —$N(R^6)$C(O)alkyl, —$N(R^6)$C(O)cycloalkyl, —$N(R^6)$C(O)aryl, —$N(R^6)$C(O)heteroaryl, —$N(R^6)$C(O)O-alkyl, —$N(R^6)$C(O)$NR^6R^7$, —$N(R^6)$S(O)$_2$alkyl, —OH, —O-alkyl, and —O-cycloalkyl;

$R^2$ is hydrogen, -alkyl, -cycloalkyl, -alkylene-cycloalkyl, -cycloalkyl, —$NR^6R^7$, -alkylene-$NR^6R^7$, -alkylene-O-alkyl, —O-alkyl, -heteroaryl, or -aryl;

$R^3$ is 1 to 6 substituents, which can be the same or different, each being independently selected from hydrogen, halogen, -alkyl, -cycloalkyl, —OH, —$OCF_3$, —$CF_3$, —O-alkyl, —O-cycloalkyl, or —$NR^6R^7$;

$R^4$ is hydrogen, -alkyl, -cycloalkyl, -aryl or -heteroaryl; or $R^3$ and $R^4$ can be joined together to form a 3 to 6 member ring;

$R^5$ is —$NR^6R^7$, —$N(R^6)$-alkylene-$NR^6R^7$, -alkyl, -cycloalkyl, -aryl, -heteroaryl, -cycloalkyl, -cycloalkylene-aryl, -alkylene-heteroaryl, -cycloalkylene-aryl, -cycloalkylene-heteroaryl, -heterocycloalkyl-aryl or -heterocycloalkyl-heteroaryl; or $R^5$ is selected from the group consisting of:

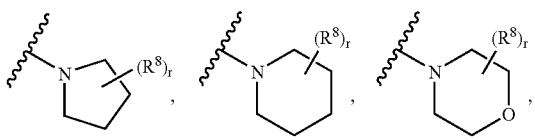

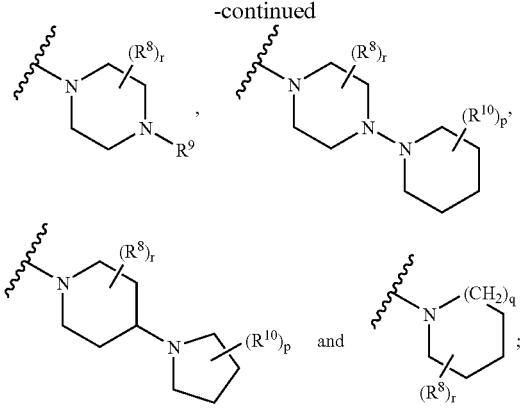

$R^6$ and $R^7$ can be the same or different, each being independently selected from the group consisting of: hydrogen, -aryl, heteroaryl, -alkyl, -cycloalkyl, -alkylene-aryl, -alkylene-heteroaryl,

r is 0, 1, 2, 3 or 4;

s is 0, 1, 2 or 3;

$R^8$ is hydrogen, —OH, alkyl, —C(O)$NR^6R^7$, —C(O)O-alkyl, or aryl, wherein said alkyl moiety may be unsubstituted or substituted with 1 to 4 hydroxy groups, and said aryl group may be unsubstituted or substituted with at least one substituent selected from the group consisting of alkyl, cycloalkyl, halogen, —$CF_3$, —$OCF_3$, —$NR^6R^7$, —CN, —$NO_2$, —$NH_2$, -alkylene-$NR^6R^7$, -alkylene-O-alkyl, —C(O)O-alkyl, —C(O)$NR^6R^7$, —$N(R^6)$C(O)alkyl, —$N(R^6)$C(O)cycloalkyl, —$N(R^6)$C(O)aryl, —$N(R^6)$C(O)heteroaryl, —$N(R^6)$C(O)O-alkyl, —$N(R^6)$C(O)$NR^6R^7$, —$N(R^6)$S(O)$_2$alkyl, —OH, —O-alkyl, and —O-cycloalkyl;

$R^9$ is selected from the group consisting of: hydrogen, alkyl, -cycloalkyl, -alkylene-aryl, -alkylene-heteroaryl, -alkyl-cycloalkyl, —C(O)O-alkyl, -alkylene-O-alkylene-OH, -aryl and -heteroaryl, wherein each said alkyl and cycloalkyl moieties may be independently substituted or unsubstituted, and if substituted then substituted with 1 to 4 hydroxy groups or at least one —$NR^6R^7$ group;

each $R^{10}$ is independently selected from hydrogen or alkyl wherein said alkyl group may be substituted or unsubstituted and if substituted then $R^{10}$ is substituted with 1 to 4 hydroxy groups;

each $R^{11}$ and $R^{12}$ are each independently selected from hydrogen, alkyl, or aryl;

p is 0, 1, 2, 3 or 4; and q is 0, 1 or 2.

2. The compound according to claim 1, wherein Ar is aryl.

3. The compound according to claim 1, wherein X=O.

4. The compound according to claim 1, wherein $R^1$ is halo.

5. The compound according to claim 1, wherein $R^2$ is H.

6. The compound according to claim 1, wherein $R^3$ is H.

7. The compound according to claim 1, wherein $R^4$ is hydrogen.

8. The compound according to claim 1, wherein $R^5$ is: $NR^6R^7$, $-NR^6$-alkylene-$NR^6R^7$,

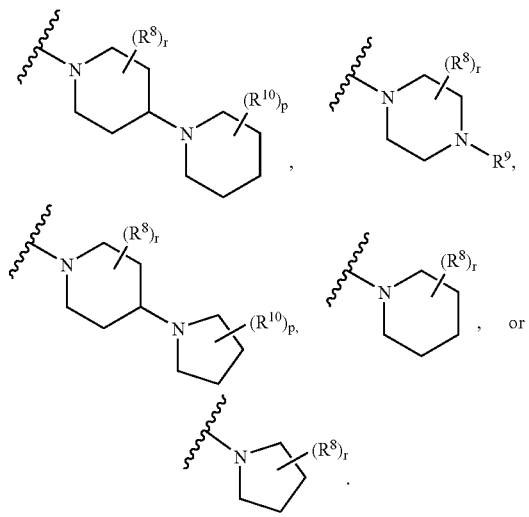

9. The compound according to claim 2, wherein Ar is phenyl.

10. The compound according to claim 7, wherein $R^4$ is $-CH_3$.

11. The compound according to claim 4, wherein $R^1$ is 4-chloro.

12. The compound according to claim 8, wherein $R^5$ is:

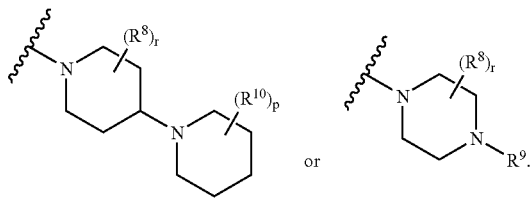

13. The compound according to claim 1, wherein:
Ar is aryl;
X=O;
$R^1$ is halo;
$R^2$ is H;
$R^3$ is H;
$R^4$ is H; and
$R^5$ is:

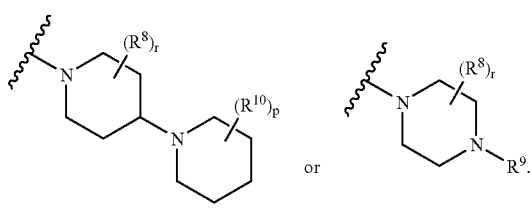

14. The compound according to claim 13 wherein one double bond is present within a bicyclic ring in the structure represented by Formula I.

15. The compound according to claim 13, wherein $R^5$ is

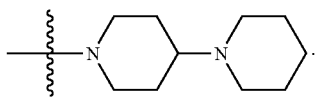

16. A compound selected from the group consisting of:

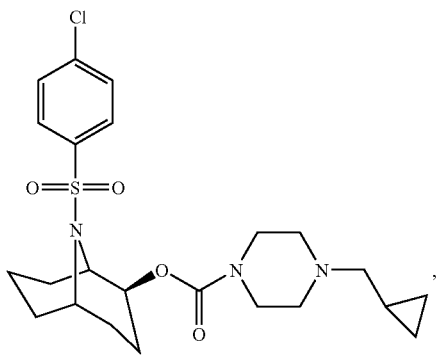

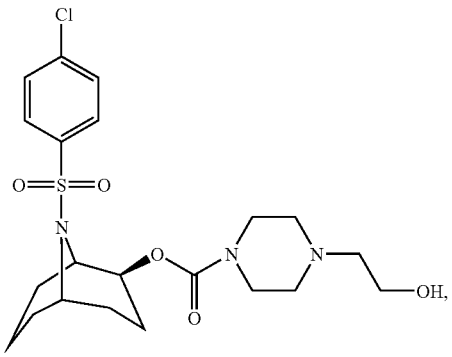

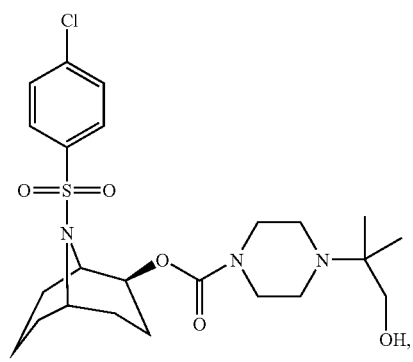

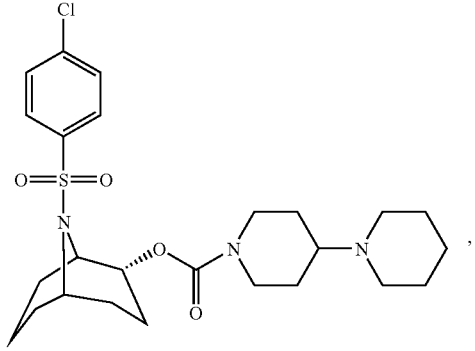

-continued
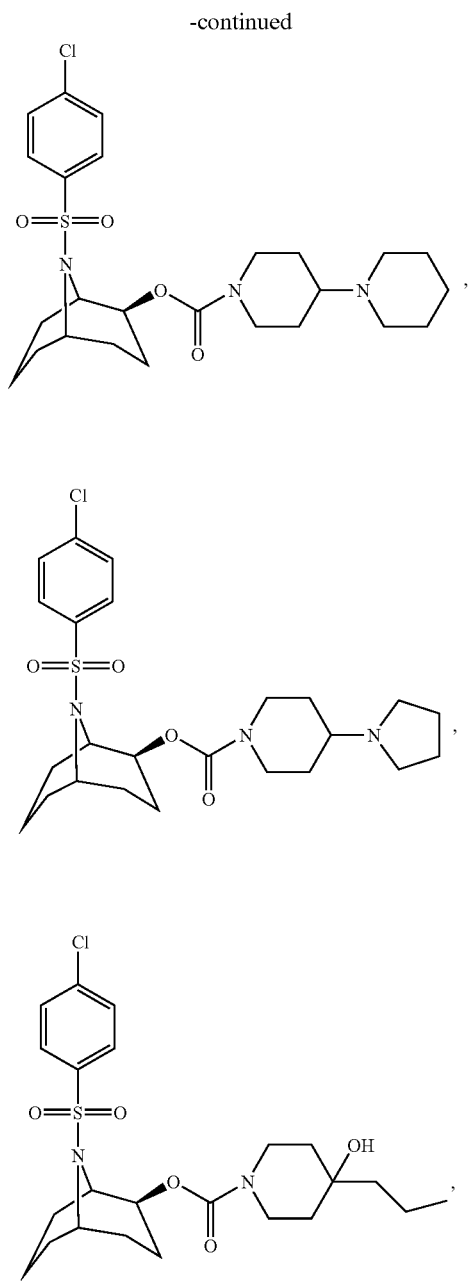
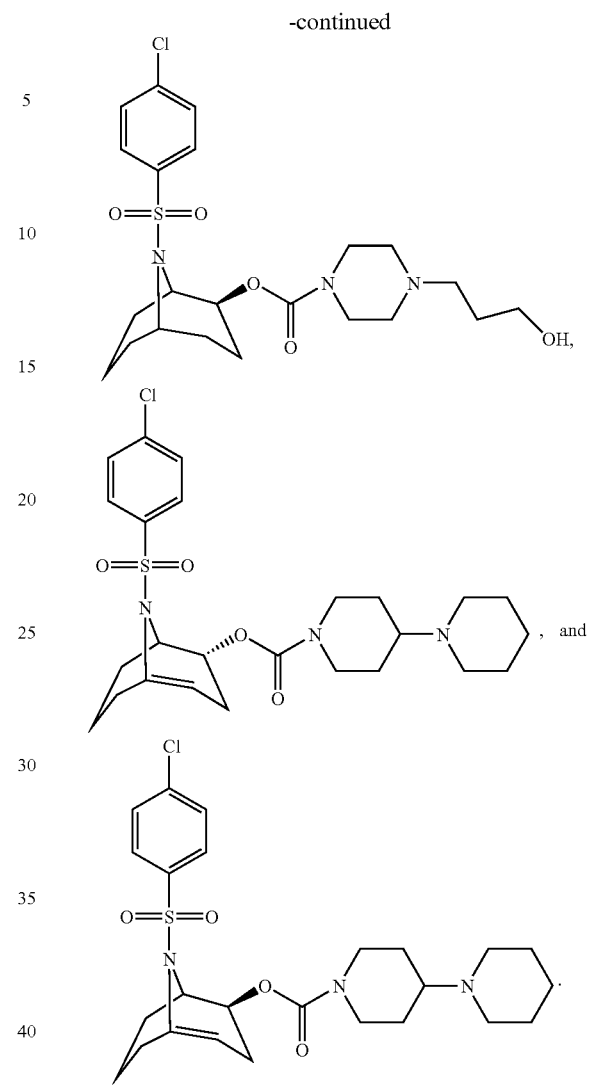
, and
17. A compound or a pharmaceutically acceptable salt and/or solvate thereof, wherein the compound has the following structure:
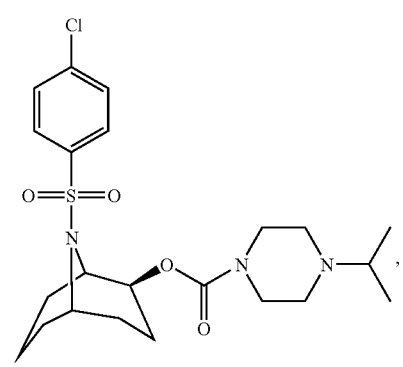
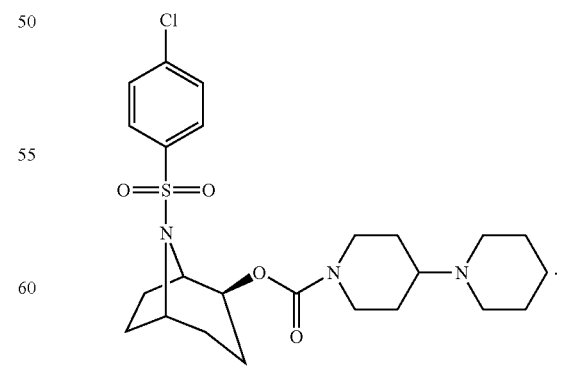
18. A compound or a pharmaceutically acceptable salt and/or solvate thereof, wherein the compound has the following structure:

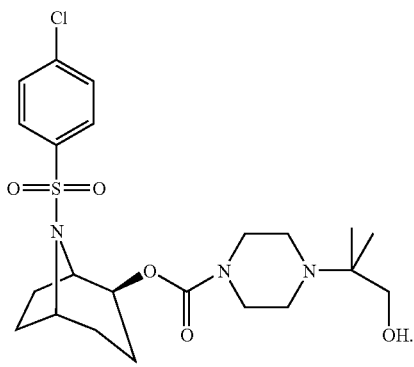

19. A compound or a pharmaceutically acceptable salt and/or solvate thereof, wherein the compound has the following structure:

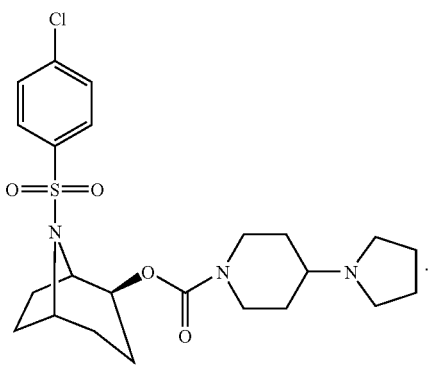

20. A compound or a pharmaceutically acceptable salt and/or solvate thereof, wherein the compound has the following structure:

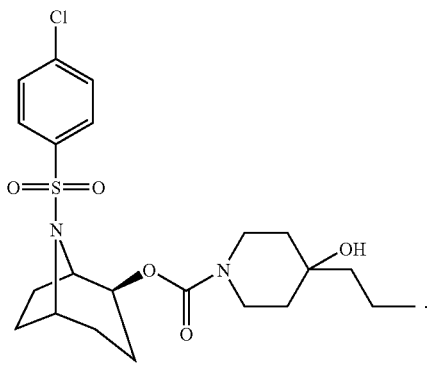

21. A compound or a pharmaceutically acceptable salt and/or solvate thereof, wherein the compound has the following structure:

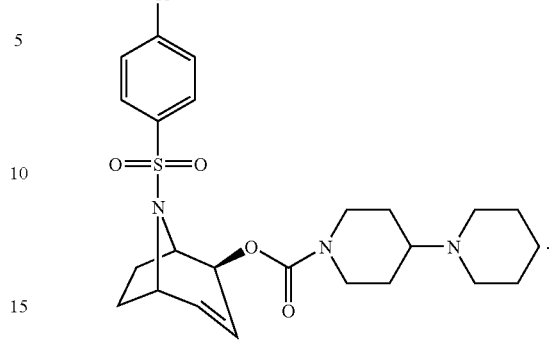

22. A compound selected from the group consisting of:

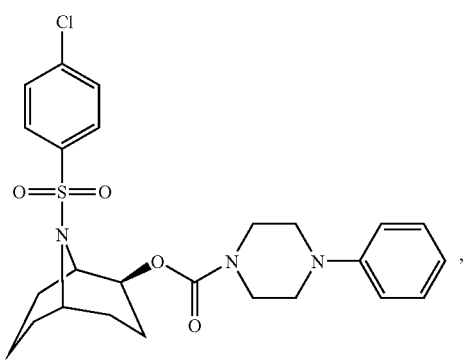

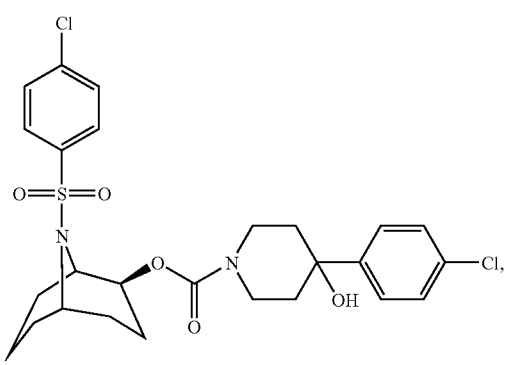

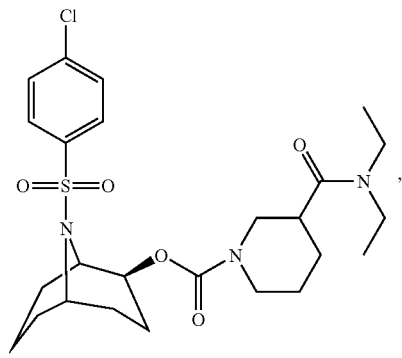

-continued
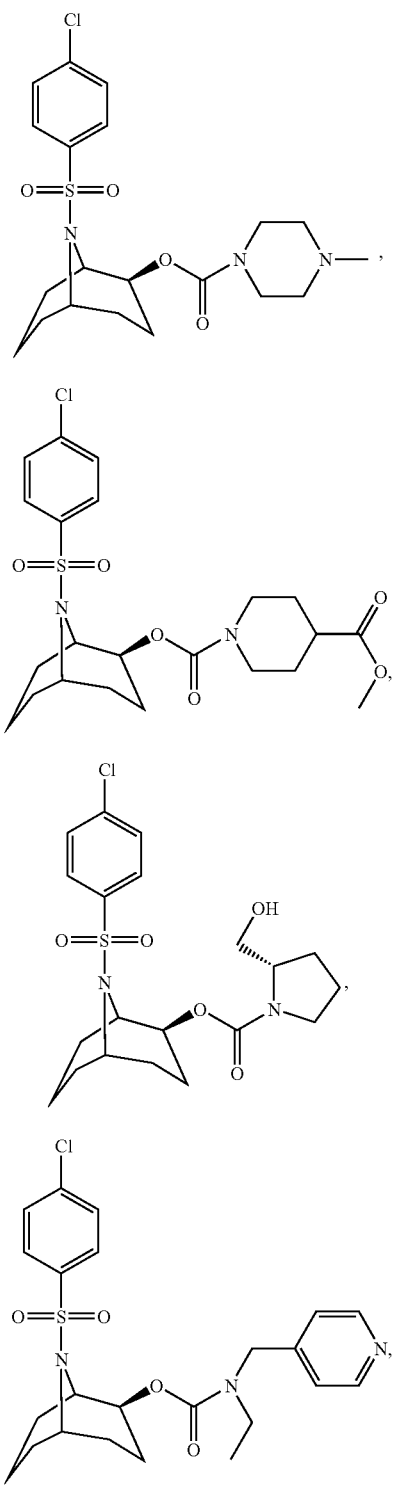
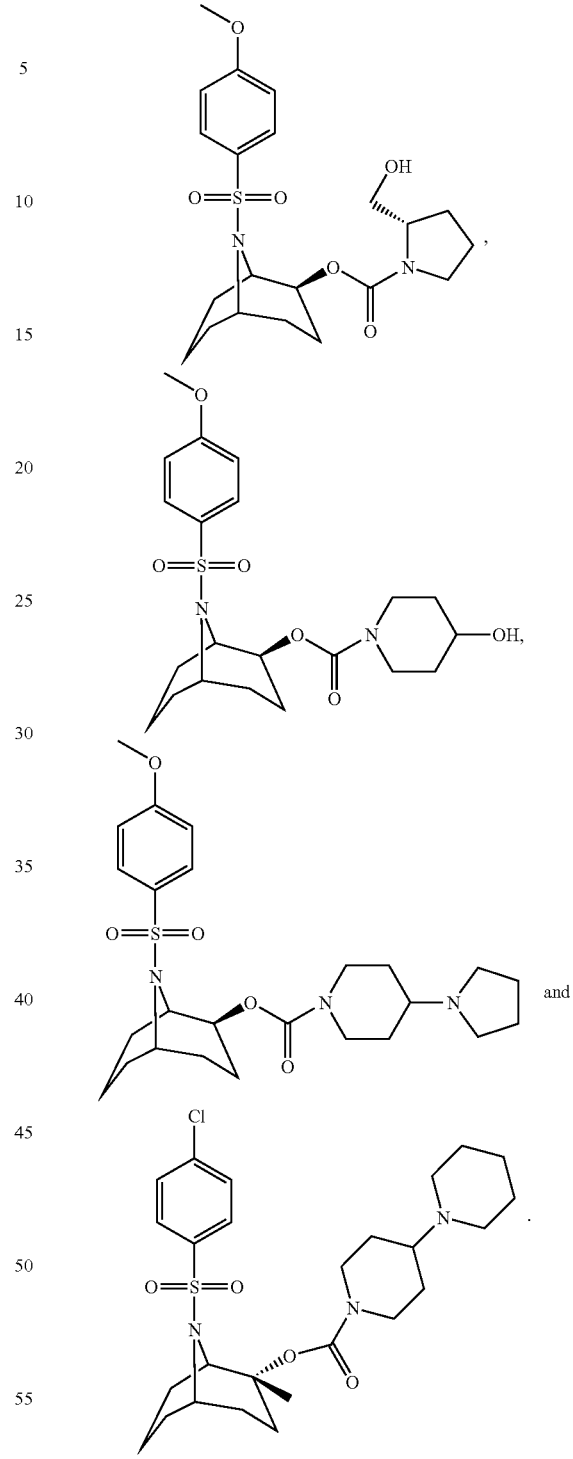
* * * * *